United States Patent
Ding et al.

(10) Patent No.: US 6,541,020 B1
(45) Date of Patent: Apr. 1, 2003

(54) METHODS AND COMPOSITIONS FOR ADMINISTRATION OF THERAPEUTIC REAGENTS

(75) Inventors: Shiulin Ding, Durham, NC (US); Kang Myung-Chol, Chapel Hill, NC (US); Thomas Michael Venetta, Raleigh, NC (US)

(73) Assignee: Trimeris, Inc., Durham, NC (US)

( * ) Notice: Subject to any disclaimer, the term of this patent is extended or adjusted under 35 U.S.C. 154(b) by 0 days.

(21) Appl. No.: 09/350,325

(22) Filed: Jul. 9, 1999

(51) Int. Cl.$^7$ ................................................. A61F 13/00
(52) U.S. Cl. ........................... 424/422; 424/486; 514/2; 514/54; 514/57; 530/323; 530/326
(58) Field of Search ................................ 424/422, 424, 424/425, 486, 499, 501; 514/2, 54, 57; 530/323, 326

(56) References Cited

U.S. PATENT DOCUMENTS

| | | | |
|---|---|---|---|
| 4,938,763 A | 7/1990 | Dunn et al. | 604/891.1 |
| 5,278,202 A | 1/1994 | Dunn et al. | 523/113 |
| 5,464,933 A | 11/1995 | Bolognesi et al. | 530/324 |
| 5,656,480 A | 8/1997 | Wild et al. | 435/325 |
| 5,702,717 A | 12/1997 | Cha et al. | 424/425 |

FOREIGN PATENT DOCUMENTS

| | | |
|---|---|---|
| WO | WO 94/28920 A1 | 12/1994 |
| WO | WO 96/19495 A1 | 6/1996 |

OTHER PUBLICATIONS

Adams JM et al., "The c–myc oncogene driven by immunoglobulin enhancers induces lymphoid malignancy in transgenic mice", Nature. 1985 Dec. 12–18;318(6046):533–8.

Alexander WS et al., "Expression of the c–myc oncogene under control of an immunoglobulin enhancer in E mu–myc transgenic mice", Mol Cell Biol. 1987 Apr.7(4):1436–44.

*Methocel Cellulose Ethers: Technical Handbook*, Jun. 1997, Form No. 192–01062–697GW, Dow Chemical Co., Midland, MI.

Fults KA and Johnston TP, "Sustained–release of urease from a poloxamer gel matrix", J Parenter Sci Technol. 1990 Mar–Apr.44(2):58–65.

Grosschedl R et al., "Introduction of a mu immunoglobulin gene into the mouse germ line: specific expression in lymphoid cells and synthesis of functional antibody", Cell. 1984 Oct.;38(3):647–58.

Hammer RE et al., "Diversity of alpha–fetoprotein gene expression in mice is generated by a combination of separate enhancer elements", Science. 1987 Jan. 2;235(4784):53–8.

Hanahan D., "Heritable formation of pancreatic beta–cell tumours in transgenic mice expressing recombinant insulin/simian virus 40 oncogenes", Nature. 1985 May 9–15;315(6015):115–22.

Johnston TP et al., "Inulin disposition following intramuscular adminstration of an inulin/poloxamer gel matrix", J Parenter Sci Technol. 1989 Nov.–Dec.;43(6):279–86.

Johnston TP et al., "Toxicological evaluation of poloxamer vehicles for intramuscular use", J Parenter Sci Technol. 1985 Mar.–Apr.;39(2):83–9.

Johnston TP et al., "Sustained delivery of interleukin–2 from a poloxamer 407 gel matrix following intraperitoneal injection in mice", Pharm Res. 1992 Mar.;9(3):425–34.

Kelsey GD et al., "Species– and tissue–specific expression of human alpha 1–antitrypsin in transgenic mice", Genes Dev. 1987 Apr.;1(2):161–71.

Kollias G et al., "Regulated expression of human A gamma–, beta–, and hybrid gamma beta–globin genes in transgenic mice: manipulation of the developmental expression patterns", Cell. 1986 Jul. 4;46(1):89–94.

Krumlauf R et al., "Developmental regulation of alpha–fetoprotein genes in transgenic mice", Mol Cell Biol. 1985 Jul.;5(7):1639–48.

MacDonald RJ, "Expression of the pancreatic elastase I gene in transgenic mice", Hepatology. 1987 Jan.–Feb.;7(1 Suppl):42S–51S.

Magram J et al., "Developmental regulation of a cloned adult beta–globin gene in transgenic mice", Nature. 1985 May 23–29;315(6017):338–40.

Mason AJ et al., "The hypogonadal mouse: reproductive functions restored by gene therapy", Science. 1986 Dec. 12;234(4782):1372–8.

(List continued on next page.)

*Primary Examiner*—Jeffrey Stucker
(74) *Attorney, Agent, or Firm*—Pennie & Edmonds LLP

(57) ABSTRACT

Methods and compositions are taught that may be used to administer specific bioactive polypeptides, known as T20 and T1249 to a patient, e.g., as a method of treating a disease or disease state. In particular, the invention teaches carrier hydrogel composition that contain (a) a polymer material and (b) an effective dose of T20, T1249 or a derivative thereof. The polymer materials used in the carrier hydrogel composition preferably have reverse gelation properties and exist as a liquid, aqueous solution at temperatures below physiological temperatures (e.g., below the body temperature of a patient) but form hydrogels under physiological conditions (e.g., at temperatures at or near the body temperature of a patient). The carrier hydrogel compositions may thus be administered to a patient by injection while they are in a liquid state. Upon administration the carrier hydrogel compositions then form hydrogels with the T20 and/or T1249 polypeptides embedded therein. The T20 and/or T1249 polypeptides are thereby released with improved pharmacokinetic properties and bioavailability. The invention thus provides methods for administering T20 and T1249 polypeptides to a patient by administering the T20 and/or T1249 polypeptides in the carrier hydrogel composition of the invention. Methods of treating various diseases and disease states, particularly HIV infection, are also provided that involve administering an effective dose of T20 and/or T1249 polypeptides to a patient in the carrier hydrogel composition of the invention.

31 Claims, 3 Drawing Sheets

OTHER PUBLICATIONS

Figure 1:
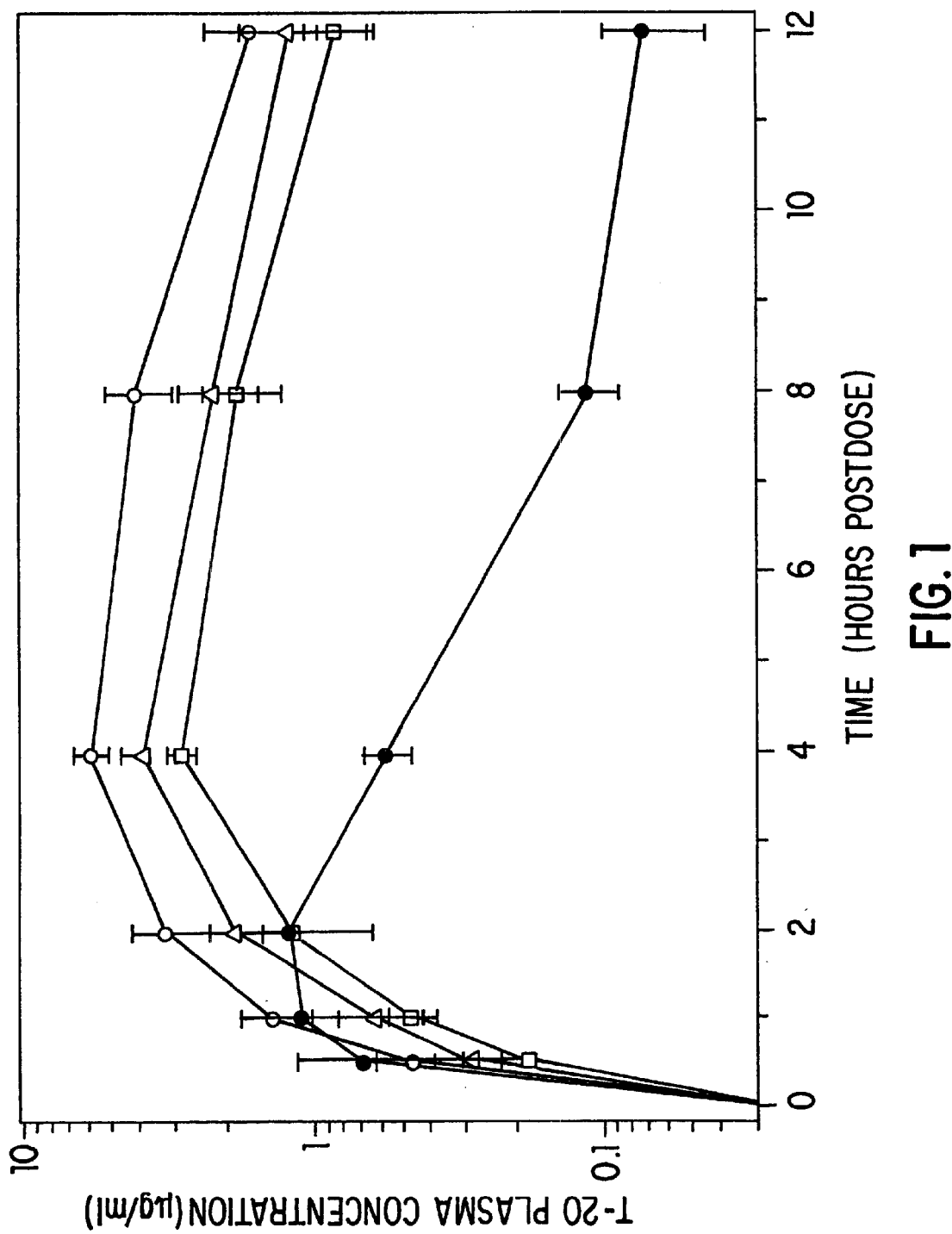

Morikawa K et al., "Enhancement of therapeutic effects of recombinant interleukin 2 on a transplantable rat fibrosarcoma by the use of a sustained release vehicle, pluronic gel", Cancer Res. 1987 Jan. 1;47(1):37–41.

Olson GL et al., "Concepts and progress in the development of peptide mimetics", J Med Chem. 1993 Oct. 15;36(21):3039–49.

Ornitz DM et al., "Elastase I promoter directs expression of human growth hormone and SV40 T antigen genes to pancreatic acinar cells in transgenic mice", Cold Spring Harb Symp Quant Biol. 1985;50:399–409.

Pinkert CA et al., "An albumin enhancer located 10 kb upstream functions along with its promoter to direct efficient, liver–specific expression in transgenic mice", Genes Dev. 1987 May;1(3):268–76.

Readhead C et al., "Expression of a myelin basic protein gene in transgenic shiverer mice: correction of the dysmyelinating phenotype", Cell. 1987 Feb. 27;48(4):703–12.

Shani M., "Tissue–specific expression of rat myosin light-–chain 2 gene in transgenic mice", Nature. 1985 Mar. 21–27;314(6008):283–6.

Swift GH et al., "Tissue–specific expression of the rat pancreatic elastase I gene in transgenic mice", Cell. 1984 Oct.;38(3):639–46.

Xu X et al., "Programmable drug delivery from an erodible association polymer system", Pharm Res. 1993 Aug.;10(8):1144–52.

METHODS AND COMPOSITIONS FOR ADMINISTRATION OF THERAPEUTIC REAGENTS

1. FIELD OF THE INVENTION

The present invention relates to compositions and methods for the administration of therapeutic reagents. In particular, the invention relates to compositions and methods for the administration of the peptides known as T20 and T1249.

2. BACKGROUND

Peptide products have a wide range of uses as therapeutic and/or prophylactic reagents for prevention and treatment of disease. For example, many peptides are able to regulate biochemical or physiological processes to either prevent disease or to provide relief from symptoms associated with disease. For example, peptides such as viral or bacterial peptides have been utilized successfully as vaccines for prevention of pathological diseases. Additionally, peptides have been successfully utilized as therapeutic agents for treatment of disease symptoms. Such peptides fall into diverse categories such as, for example, hormones, enzymes, immunomodulators, serum proteins and cytokines.

For peptides to manifest their proper biological and therapeutic affect in patients, they must be present in appropriate concentrations at their sites of action in vivo. More specifically, the pharmacokinetics of any particular compound, including any particular peptide, is dependent on the bioavailability, distribution and clearance of that compound in vivo. However, the chemical nature and characteristics of peptides, such as size, complexity, conformational requirements and solubility profiles, tend to cause peptides to have pharmakokinetic profiles that are suboptimal compared to the pharmakokinetic profiles of other compounds.

Accordingly, there has been considerable effort in the art to attempt to develop ways to administer therapeutic reagents such as peptides so that both the bioavailability and the half-life of the therapeutic reagents are increased. For example, drug loaded biodegradable controlled release devices fabricated from polyglycolic acid (PGA) and polylactic acid (PLA) polymers have been described. One such device, the Lupron Depot™, consists of injectable microcapsules which release a therapeutic reagent, leuprolide acetate, over a prolonged period of time (e.g., about 30 days). However, due to the hydrophobic properties of these polymers, drug loading and device manufacturing using these methods requires organic solvents such as methylene chloride, chloroform, acetic acid or dimethyl formamide, which may induce tissue irritation in patients. Further, the final product requires extensive drying and exists as a distinct solid shape. Thus, such devices must be administered either as implants or injected as solid microspheres. Such solid dosage forms may cause additional tissue irritation, and administration as implants requires invasive surgery. In addition, hydrophilic molecules such as certain peptides cannot diffuse out through the hydrophobic matrix of these materials.

Injectable systems for delivering therapeutic reagents such as peptides have also been proposed. For example, Dunn et al., U.S. Pat. Nos. 4,938,763 and 5,278,202, describe thermoplastic and/or thermosetting polymer systems which may be mixed with a drug injected in a liquid form and which, upon injection and exposure to body fluids or water, coagulate into a gel polymer matrix encapsulating the drug. The gel polymer matrix releases the drug in a controlled manner and degrades to products that are readily metabolized and excreted. However, the solutions require the use of organic solvents, such as N-methyl-2-pyrrolidone, methyl ethyl ketone, dimethylformamide, propylene glycol, THF, DMSO, dodecylazacycloheptan-2-one and the like, that may be toxic or irritating to body tissues. Further, preparation of these systems is quite complicated and unwieldily; the drug must be admixed with the prepolymer solution followed by addition of a curing reagent. The preparation must be injected almost immediately after the addition of the curing reagent and cannot be stored.

Cha et al., U.S. Pat. No. 5,702,717, also describes an injectable system and method for delivering drugs, including peptides, dissolved or dispersed in a biodegradable block copolymer that has a reverse gelation temperature below the physiological temperature of a patient. Specifically, the copolymer consist of a hydrophobic polymer block composed of poly($\alpha$-hydroxy acids) or poly(ethylene carbonates), and a hydrophilic polymer block composed of polyethylene glycol. The composition may be loaded with a drug and stored as a liquid at a temperature below its gelation temperature. However, upon injection into a patient, the temperature is increased and the composition undergoes a phase change to form a hydrogel.

Poloxamer compounds, which are block copolymer systems composed of two different polymer blocks, i.e., hydrophilic poly(ethylene oxide) blocks and hydrophobic poly(propylene oxide) blocks, are also known and may be used to administer certain compounds. These polymer blocks are synthesized to make a triblock of poly(ethylene oxide)-poly(propylene oxide)-poly(ethylene oxide) and marketed under the Pluronic™ tradenames. The compositions known as Pluronic F-127™ or Poloxamer 407™ is of particular interest for drug delivery. Pluronic F-127™ consists of approximately 70% ethylene oxide and 30% propylene oxide by weight, and has an average molecular weight of 11500. The copolymer has reverse thermal gelation properties, and is liquid at low temperature (under 10° C.) while forming a soft gel at physiological temperatures. Studies have been performed to investigate whether Pluronic F-127™ gels may be utilized as an injectable sustained release depot (see, e.g., Johnson et al., 1985, *J. Parenteral Sci. & Tech.* 39:83–88; Fults and Johnson, 1990, *J. Parenteral Sci. & Tech.* 44:58–65; Johnson et al., 1992, *Pharmaceutical Research* 9:425–434; Morikawa et al., 1987, *Cancer Res.* 47:37–41; and Johnson and Miller, 1989, *J. Parental Sci. & Tech.* 43:279–285; Xu et al., 1993, *Pharmaceutical Research* 10:1144–1152).

3. SUMMARY OF THE INVENTION

The present invention provides, first, carrier hydrogel compositions which may be used to administer bioactive molecules to a patient. Specifically, the carrier hydrogel compositions of the invention are compositions comprising a polymer material that forms a hydrogel at physiological temperatures and a polypeptide which is either T20 or T1249. The carrier hydrogel compositions of the invention are ideally suited for administering the specific peptides, referred to as T20 and T1249, which are described herein, as well as derivatives of the T20 and T1249 peptides described herein.

The carrier hydrogel compositions comprise gelling materials that possess a reverse thermal gelation property, and at least one peptide, i.e., T20, T1249 or a derivative thereof.

The carrier hydrogel compositions exist as liquid, aqueous solutions at temperatures that are below physiological temperatures. However, when the gelling materials are exposed to physiological temperatures (e.g., temperatures of about 37° C.) they form a polymer gel which is biodegradable or at least bioerodible. Such carrier hydrogel compositions can be stored indefinitely in an aqueous state. The carrier hydrogel composition can then be administered to a patient in liquid form, e.g., by subcutaneous injection. Upon administration, the carrier hydrogel composition is heated to the patient's body temperature and forms a polymer gel which then acts as a sustained-release matrix for the peptides.

The carrier hydrogel compositions of the invention contain at least one polymer material in sufficient amounts (i.e., at sufficient concentrations in an aqueous solution) to form a gel. Preferably, the polymer material is Poloxamer 407™ or Methyl cellulose. The carrier hydrogel compositions of the invention also contain a T20 or T1249 peptide, or a derivative thereof, e.g., for administration to a patient. Preferably, the carrier hydrogel compositions of the invention contain a sufficient concentration of peptide such that an effective dose of the peptide is released.

The invention is based, at least in part, on the unexpected discovery that significantly improved pharmacokinetic profiles, including increased half life and reduced clearance rates, are achieved when T20 and/or T1249 peptides are administered in the carrier hydrogel compositions of the present invention relative to administration by intravenous injection of the peptides in aqueous solution. Accordingly, the invention also provides methods for administering T20 and/or T1249 peptides to a patient. The methods of the invention comprise administering to a patient a carrier hydrogel composition that contains (a) gelling materials that possess a reverse thermal gelation property, and (b) at least one peptide, i.e., T20, T1249 or a derivative thereof.

As used herein, the following terms shall have the below assigned meanings:

"Patient," as used herein, refers to any individual organism, most preferably a human or other mammal, to which bioactive molecules are administered. Most preferably, bioactive molecules are administered to a patient to cure, ameliorate or prevent a symptom of a particular disease or disease state. However, as the term is used herein, a patient may also be an individual organism, most preferably a human or other mammal, to which bioactive molecules are administered for some other purpose, such as to prevent disease, e.g., by vaccination, or by directly blocking pathogen (e.g., viral) infection or pathogen induced cell fusion; or for medical diagnostics and/or prognostics. A patient may also be an individual in whom some molecular and/or biochemical process, e.g., fusogenic events, may be modulated by administering bioactive molecules such as peptides.

"Peptides" and "polypeptides" are defined herein as organic compounds comprising two or more amino acids covalently joined by peptide bonds. Peptides may be referred to with respect to the number of constituent natural L-amino acids, i.e., a dipeptide contains two amino acid residues, a tripeptide contains three amino acid residues, etc. Peptides may also include non-natural amino acids and any of the modifications and additional amino and carboxyl groups as are described herein. Peptide sequences defined herein are represented by the one-letter amino acid code as follows:

| A | (alanine) | L | (leucine) |
|---|---|---|---|
| R | (arginine) | K | (lysine) |
| N | (asparagine) | M | (methione) |
| D | (aspartic acid) | F | (phenylalanine) |
| C | (cysteine) | P | (proline) |
| Q | (glutamine) | S | (serine) |
| E | (glutamic acid) | T | (threonine) |
| G | (glycine) | W | (tryptophan) |
| H | (histidine) | Y | (tyrosine) |
| I | (isoleucine) | V | (valine) |
| L | (leucine) | X | (any amino acid) |
| K | (lysine) | | |

An "effective dose" refers to a quantity of a bioactive molecule, e.g., a peptide, that is sufficient to produce a biological effect in an organism. In instances wherein the bioactive molecules are administered as therapeutic reagents, an effective dose is defined as a "therapeutically effective dose." A "therapeutically effective dose" refers to a quantity of bioactive molecules, e.g., peptides, that is sufficient to cure, prevent or ameliorate a disease or disease state, or to prevent or ameliorate one or more symptoms of a disease or disease state. Prevention is understood to include prevention or inhibition of pathogen (e.g., viral) infection, or prevention or inhibition of viral-induced events such as cell-fusion. With respect to the carrier hydrogel compositions of the invention, the peptide concentration should be sufficient for an effective dose or therapeutically effective dose to be released from the composition once the composition is administered.

"Gel" and "hydrogel" are interchangeable terms and are defined herein as a semi-solid combination of one or more of the gel-forming polymers described herein. It is understood that one skilled in the art will readily recognize a hydrogel, e.g., as a composition which does not flow under 1 g gravitational pull or, in the case of a "soft" hydrogel, which flows only at a very slow rate (i.e., less than 1–10% the flow rate of the solution state of the polymer).

"Solution," and "aqueous solution" are defined herein as water-based liquids (including viscous liquids). In particular, a "gel solution" or "aqueous gel solution" is defined herein to comprise one or more gel-forming polymer materials in aqueous solution at sufficient amounts (i.e., sufficient concentration) to form a gel.

The terms "lower critical solution temperature" or "LCST," "gelation temperature" and "reverse thermal gelation temperature" or "RTGT" are defined herein to mean the temperature at which a gel solution undergoes reverse thermal gelation to form a gel or hydrogel. In particular, LCST, gelation temperature or RTGT refer to the temperature below which the gel-forming polymer materials exist in an aqueous gel solution and above which the polymer material form a hydrogel.

4. BRIEF DESCRIPTION OF THE DRAWINGS

FIG. 1 shows a plot of T20 blood plasma concentrations in Sprague Dawley rats over a 12 hour time period postdose for T20 polypeptide administered in a hydrogel or in aqueous solution; Group I: (—○—), 50 mg/mL T20 in high viscosity hydrogel; Group II: (—□—),25 mg/mL T20 in high viscosity hydrogel; Group III: (—△—), 25 mg/mL T20 in lower viscosity hydrogel; Group IV: (—●—), 25 mg/mL T20 in aqueous buffer.

Figure 2:
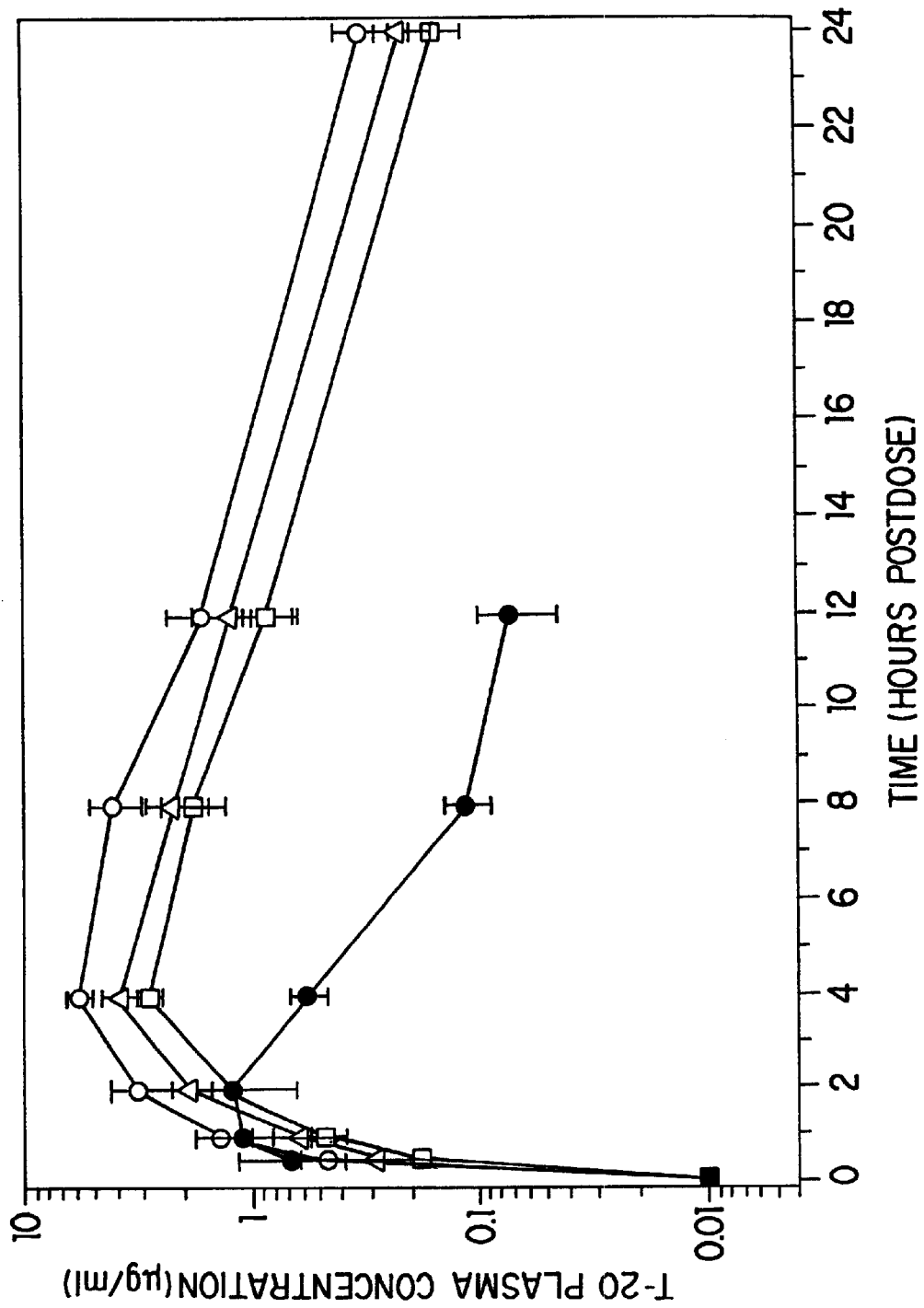

FIG. 2 shows a plot of T20 blood plasma concentrations in Sprague-Dawley rats over a 24 hour time period postdose for T20 polypeptide administered in various hydrogel compositions; Group I: (—○—), 50 mg/mL T20 in high viscosity hydrogel; Group II: (—□—), 25 mg/mL T20 in high viscosity hydrogel; Group III: (—△—), 25 mg/mL T20 in lower viscosity hydrogel; Group IV: (—●—), 25 mg/mL T20 in aqueous buffer.

Figure 3:
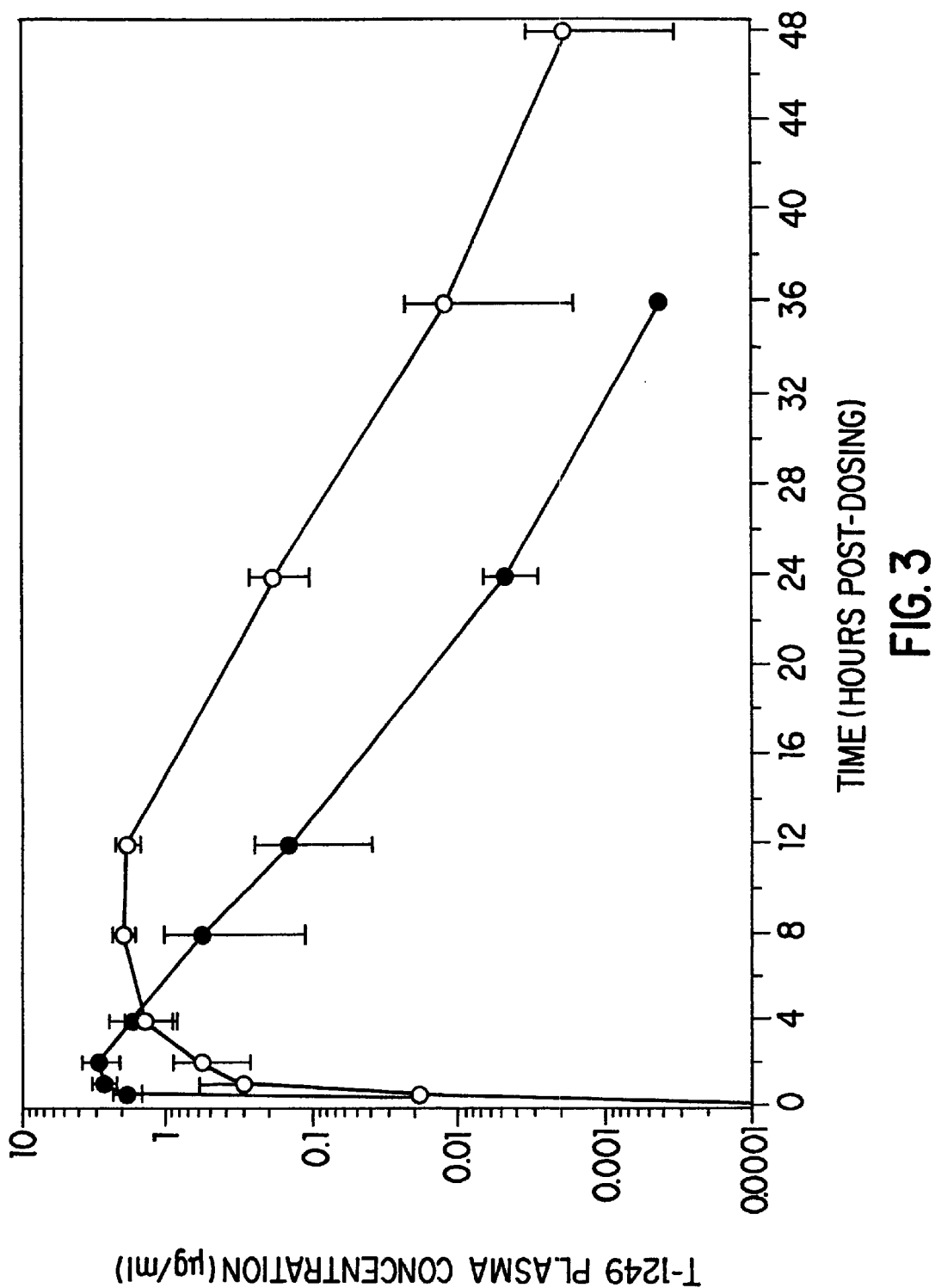

FIG. 3 shows a plot of T1249 blood plasma concentrations in Sprague-Dawley rats for T1249 administered in a hydrogel and in aqueous solution; Group I: (—○—), 12.5 mg/mL T1249 in hydrogel; Group II: (—●—), 12.5 mg/mL T1249 in aqueous buffer.

5. DETAILED DESCRIPTION OF THE INVENTION

Described herein are novel carrier hydrogel compositions which may be used to administer bioactive peptides to a patient. In particular the novel carrier hydrogel composition of the invention are useful for administering the peptides referred to herein as T20 and T1249, as well as derivatives of these peptides, to a patient. Also described herein are methods for using the carrier hydrogel compositions of the invention to administer these bioactive molecules to a patient. The carrier hydrogel compositions of the invention comprise (a) at least one hydrogel material and (b) T20, T1249, and/or a T20 or T1249 derivative. The carrier compositions of the invention preferably form hydrogels at physiological temperatures (e.g., at temperatures between about 25 and 40° C., including temperatures of about 37° C. or at or near the body temperature of a patient), but are liquid at temperatures below temperature (e.g., at or below room temperature, at or below 25° C., at or below 20° C., at or below 15° C., at or below 10° C., or at or below 5° C.

Polymer materials that may be used for the novel carrier hydrogel compositions of the invention are described in detail in Section 5.1 below. Section 5.2 and its subsections describe the bioactive peptides, i.e., T20, T1249, T20 and T1249 derivatives, that may be administered by and used in the carrier hydrogel composition of the invention, as well as methods of synthesizing such peptides. The carrier hydrogel compositions can further comprise, for example, additional components as described below in Section 5.3. Section 5.4, below, describes such methods of using the carrier compositions of the invention.

Further, the examples presented in Sections 6–8 herein below describe specific exemplary and non-limiting embodiments of the invention. In particular, the example presented in Section 6 describes the synthesis and characterization of several specific embodiments of the carrier hydrogel compositions of the invention. The examples presented in Sections 7 and 8 describe the use of specific carrier hydrogel compositions of the invention to administer T20 and T1249 in vivo, and demonstrate that peptides administered by these compositions have improved pharmacokinetic properties, including increased half-life and bioavailability, relative to administration of T20 and T1249 by traditional means, e.g., by intravenous injection of T20 or T1249 in aqueous solution.

The descriptions and examples presented herein below are by way of example and not by way of limitation. Related variants and equivalents of the specific embodiments described herein will be apparent to one of skill in the art. Such variants and equivalents are also intended to be encompassed by the pending claims.

5.1. CARRIER HYDROGEL MATERIALS

The polymer material used in the compositions is a polymer material that forms a hydrogel. In particular, the polymer material solutions possess a reverse thermal gelation property. That is, aqueous solutions of the polymer material exist in a liquid state at temperatures below a "gelation temperature." At temperatures at or above the gelation temperature, aqueous solutions of the polymer material exist as a hydrogel. Most preferably, the gelation temperature of the polymer material is such that the material exists as a hydrogel at physiological temperatures, i.e., at the body temperature of a warm blooded organism to which the carrier hydrogel composition of the invention are administered (e.g., 37° C.), yet exists in a liquid state below the physiological temperature. For example, aqueous solutions of the carrier hydrogel compositions of the present invention preferably form a hydrogel at temperatures of at least about 37° C. or above, or at least about 30° C. or above, while existing in a liquid state at cooler temperatures, e.g., at about 25° C. and below. Preferably, the hydrogel compositions of the invention are liquid at temperatures below 25° C., below 20° C., below 15° C., below 10° C., or below 4–5° C.

Preferably, the polymer material is Poloxamer 407™ (Pluronic F-127™, BASF Company, Wyandotte, Mich.) or Methyl cellulose (Methocel™ A, Dow Chemical Company, Midland, Mich.). However, other polymer materials may be used, including but not limited to hydroxypropylmethylcellulose and sodium carboxymethylcellulose, and konjac to name a few.

Poloxamer 407™ is a block polymer composed of two different polymer blocks: hydrophilic poly(ethylene oxide) blocks and hydrophobic poly(propylene oxide) blocks. These two compositions are combined to form a triblock of poly(ethylene oxide)-poly(propylene oxide)-poly(ethylene oxide). Solutions of these triblock polymers undergo solidification or gelation as the temperature of the solution is raised above a critical temperature, known as the gelation temperature. Aqueous solutions of these polymers form micelles (microscopic spheres incorporating water) at low concentrations, and turn into thick continuous gels at higher concentrations (e.g., approximately 20–30% by weight) and elevated temperature (e.g., approximately 30° C.).

In particular, Poloxamer 407™ consists of approximately 70% poly(ethylene oxide) and 30% poly(propylene oxide) by weight, and has an average molecular weight of 11500 Da. Concentrated solutions (e.g., of ~20–30% by weight) are fluid at low temperatures (e.g., below 10° C.) but are a hydrogel a body temperature.

Methyl cellulose, the methyl ether derivative of cellulose, is another polymer well known in the art whose aqueous solutions possess a reverse thermal gelation property. Methylcellulose is generally regarded as a safe material and is commonly used in solid dosage forms for oral administration such as sustained release tablets (see, e.g., the Dow Technical Handbook for Methocel, 1996, Form No. 192-01062-996GW, Dow Chemical Co., Midland, Mich.).

Preferably, the polymer material is present in the carrier hydrogel composition of the invention at sufficient concentrations so that the compositions have a reverse gelation property and form hydrogels when heated to temperatures at or below physiological temperature. In those embodiments of the invention where the polymer material is Poloxamer 407™, the material is preferably present at concentrations from about 15% to about 35% by weight (before addition of the peptide). More preferably, the material is present at concentrations from about 20% to about 30% by weight (before addition of the peptide). Other concentrations will be apparent to those skilled in the art depending on the particular circumstances and/or applications for which the invention is used, including, e.g., the particular peptides or peptide derivatives to be administered and the particular organism (i.e., the patient) to which the peptides or peptide derivatives are to be administered.

In those embodiments of the invention where the polymer material is methyl cellulose, the material is preferably present at concentrations from about 1% to about 10% by weight (before addition of the peptide). More preferably, methyl cellulose is present at concentrations from about 4% to about 8% by weight. Most preferably, methyl cellulose is present in the carrier hydrogel composition at a concentration of about 5% by weight.

5.2. T20 AND T1249

The carrier hydrogel compositions of the invention are particularly useful for administering bioactive peptides known in the art as T20 and T1249, as well as for administering derivatives of the T20 and T1249 peptides. Administration of T20 or T1249 in the carrier hydrogel composition of the present invention results in improved pharmacokinetic properites, including increase bioavailability and half-life, of the peptide relative to administration by methods currently known in the art, e.g., intravenous injection of T20 or T1249 in aqueous solution. Accordingly, the carrier hydrogel compositions of the invention preferably contain an effective dose (or a therapeutically effective dose) of T20, T1249 or a derivative thereof (i.e., a derivative of T20 or T1249) to be released from the carrier hydrogel composition once it is administered to a patient. For example, in preferred embodiments the concentration of T20 or T1249 is between about 1 mg/mL and 100 mg/mL, more preferably between 10 mg/mL and 100 mg/mL.

5.2.1. T20 AND T1249 PEPTIDES AND DERIVATIVES

The polypeptides referred to herein as T20 and T1249 are known peptides which have potent antiviral properties. In particular, T20 and T1249 possess potent activity against HIV and are useful, therefore, in methods of treating, inhibiting and/or preventing HIV infection.

The peptide T20 is a polypeptide also known in the art as DP178 that is described, e.g., in U.S. Pat. No. 5,464,933, which is incorporated herein by reference in its entirety. In particular, T20 is polypeptide corresponding to the following 36 amino acid sequence of the HIV-$1_{LAI}$gp41 protein (amino acid residues 638 to 673):

YLTSLIHSLIEESQNQQEKNEQELLELD-KWASLWNWF (SEQ ID NO.:1).

The T20 peptide is preferably blocked at the amino terminus by an acetyl group (Ac) and at the carboxyl terminus by an amido group ($NH_2$).

T1249 sequences are described and enabled, in general, herein below. In particular, T1249 is a 39 amino acid peptide having the sequence:

WQEWEQKITALLEQA-QIQQEKNEYELQKLDKWASLWEWF (SEQ ID NO.:2).

Like T20, T1249 is preferably blocked at the amino terminus by an acetyl group (Ac) and at the carboxyl terminus by an amido group ($NH_2$). Both T20 and T1249 peptides exhibit potent antiviral activity in vitro as well as in vivo. In particular, both peptides exhibit anti-HIV activity. T1249 additional exhibits, e.g., anti-SIV (simmian immunodeficiency virus) activity.

It is understood that the polypeptides which may be used in the compositions of the present invention are not limited to the particular T20 and T1249 amino acid sequences recited in SEQ ID NOS. 1 and 2 above, but also include derivatives of T20 and T1249. Derivatives of T20 and T1249 include, for example, polypeptides whose amino acid sequences are derived from, but are not necessarily identical to, the amino acid sequences depicted in SEQ ID NOS. 1 and 2, above. T20 and T1249 derivatives further include, but are not limited to, peptides or peptide derivatives that comprise one or more amino acid residues that are not genetically encoded and/or are not naturally occurring. Such T20 and T1249 derivatives may include, for example, peptide derivatives that incorporate one or more amino acid analogs.

Accordingly, the T20 and T1249 polypeptides which may be used in the present invention further include peptide sequences comprising amino acid sequences that are otherwise identical to the amino acid sequences provided in SEQ ID NOS. 1 and 2 above, but comprise one or more amino acid substitutions, additions or deletions (for example, amino- or terminal- insertions and truncations). With respect to amino acid residue insertions, preferably insertions are no greater than about 50 amino acid residues, and more preferably no more than about 15 amino acid residues. With respect to amino acid deletions, it is generally preferably the T20 and T1249 polypeptides used in the carrier hydrogel composition of the invention be at least about 4–6 amino acid residues in length.

Preferred amino and/or carboxy terminal insertions include ones which comprise amino acid sequences amino and/or carboxy to the endogenous protein sequence from which the T20 or T1249 polypeptide is derived. For example, in the case of T20, such an insertion would comprise an amino and/or carboxy-terminal insertion comprising a gp41 amino acid sequence adjacent to the gp41 sequence of the polypeptide (e.g., the T20 sequence: amino acid residues 638 to 673 of gp41).

It is understood that certain amino acid residues in the T20 and T1249 polypeptide sequences depicted in SEQ ID NOS. 1 and 2 can be replaced with other amino acid residues without significantly deleteriously affecting, and in some instances even enhancing, the activity of the peptides. Thus, the T20 and T1249 polypeptides which may be used in, and are therefore considered part of, the carrier hydrogel composition of the present invention include altered forms of the T20 and T1249 amino acid sequences disclosed herein (i.e., SEQ ID NOS. 1 and 2) wherein at least one defined amino acid residue in the structure (i.e., in the sequence) is substituted with another amino acid residues. Such amino acid substitutions may be conservative, i.e., the replacing amino acid residue has physical and chemical properties (e.g., similar charge, size and/or hydrophobicity characteristics) that are similar to the amino acid residue being replaced, or non-conservative amino acid substitutions.

In addition, the amino acid substitutions need not be, and in certain embodiments preferably are not, restricted to the genetically coded amino acids. Indeed, the T20 and T1249 polypeptides may contain amino acid residues and/or amino acid analogs that are not genetically encoded. Thus, in addition to the naturally occurring genetically encoded amino acids, amino acid residues in the polypeptides may be substituted with naturally occurring non-encoded amino acids and synthetic amino acids.

Certain commonly encountered amino acids which provide useful substitutions include, but are not limited to, β-alanine (β-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); naphthylalanine (Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,3-diaminobutyric acid (Dab); p-aminophenylalanine (Phe(pNH$_2$)); N-methyl valine (MeVal); homocysteine (hCys), homophenylalanine (hPhe) and homoserine (hSer); hydroxyproline (Hyp), homoproline (hPro), N-methylated amino acids and peptoids (N-substituted glycines).

While in most instances, the amino acids of the T20 or T1249 polypeptide will be substituted with L-enantiomeric amino acids, the substitutions are not limited to L-enantiomeric amino acids. Thus, also included in the definition of "mutated" or "altered" forms are those situations where an L-amino acid is replaced with an identical D-amino acid (e.g., L-Arg→D-Arg) or with a D-amino acid of the same category or subcategory (e.g., L-Arg→D-Lys), and vice versa.

It is to be understood that the present invention also contemplates T20 and T1249 polypeptide analogues wherein one or more amide linkage is optionally replaced with a linkage other than amide, preferably a substituted amide or an isostere of amide. Thus, while the amino acid residues within T20 and T1249 are generally described in terms of amino acids, and preferred embodiments of the invention are exemplified by way of peptides, one having skill in the art will recognize that in embodiments having non-amide linkages, the term "amino acid" or "residue" as used herein refers to other bifunctional moieties bearing groups similar in structure to the side chains of the amino acids. In addition the amino acid residues may be blocked or unblocked.

Additionally, one or more amide linkages can be replaced with peptidometic or amide mimetic moieties which do not significantly interfere with the structure or activity of the polypeptides. Suitable amid mimetic moieties are described, for example, in Olson et al., 1993, *J. Med. Chem* 36:3049.

Preferably, the T20 and T1249 polypeptides depicted in SEQ ID NOS. 1 and 2 above have specifically modified or blocked amino and/or carboxy termini. In particular, preferably the amino termini are block by an acetyl group (Ac) and the carboxy termini are blocked by an amido group (NH$_2$). However, any polypeptide comprising an unmodified primary amino acid sequences as depicted in SEQ ID NOS. 1 and 2 is considered to be a T20 or T1249 polypeptide and may also be used in the present invention. The amino-and/or carboxy-termini of the polypeptides can therefore comprise an amino group (—NH$_2$) or a carboxy group (—COOH), respectively. Alternatively, the polypeptides' amino termini may, for example, represent a hydrophobic group, including but not limited to carbobenzyl, dansyl, T-butoxycarbonyl, decanoyl, napthoyl or other carbohydrate groups; an acetyl group; 9-fluorenylmethoxy-carbonyl (FMOC) group; a macromolecular carrier group; or a modified, non naturally occurring amino acid residue. Alternatively, the polypeptides' carboxy terminui can, for example, represent an amido group; a T-buxoxycarbonyl group; a macromolecular carrier group; or a modified non-naturally occurring amino acid residue.

The T20 and T1249 polypeptides which may be used in the methods and compositions of the present invention also include "hybrid polypeptides." Such T20 and T1249 hybrid polypeptides generally comprise a core polypeptide and at least one "enhancer" sequence which may be used to enhance the pharmacokinetic properties of the resultant hybrid polypeptide.

Possible core polypeptides include the T20 polypeptide sequence depicted in SEQ ID NOS. 1, above, or the T1249 core polypeptide sequence:

TALLEQAQIQQEKNEYELQKLDK (SEQ ID NO.:3)

as well as any derivative of the T20 polypeptide sequence depicted in SEQ ID NO.:1 or of the T1249 core polypeptide sequence depicted in SEQ ID NO.:3.

Possible enhancer sequences include, but are not limited to, the following amino acid sequences (in forward or reverse orientation): "WXXWXXXI", "WXXWXXX", "WXXWXX", "WXXWX", "WXXW", "WXXXWXWX", "XXXWXWX", "XXWXWX", "XWXWX", "WXWX", "WXXXWXW", "WXXXWX", "WXXXW", "IXXXWXXW", "XXXWXXW", "XXWXXW", "XWXXW", "XWXWXXXW", "XWXWXXX", "XWXWXX", "XWXWX", "XWXW", "WXWXXXW", or "XWXXXW", wherein X can be any amino acid, W represents tryptophan and I represents isoleucine.

Typically, an enhancer peptide sequence will be about 4, 5, 6, 7, 8, 9, 10, 11, 12, 13, 14, 15, 16, 17, 18, 19, 20, 21, 22, 23, 24, 25, 26, 27, 28, 29 or 30 amino acid residues in length, with about 4 to about 20 residues in length being preferred, about 4 to about 10 residues in length being more preferred, and about 6 to about 8 residues in length being most preferred. Among the most preferred enhancer peptide sequences are ones comprising the amino acid sequences "WQEWEQKI" (SEQ ID NOS:19). and "WASLWEWF (SEQ ID NO:23)" However, Table II, below, depicts, by way of example and not by way of limitation, additional preferred enhancer peptide sequences which may be used in polypeptides administered by the methods and compositions of the present invention (SEQ ID NOS:4–48). It is to be understood that while the forward orientation of these sequences is depicted below, the reverse orientation of these sequences may also be used as enhancer peptide sequences in polypeptides used in the present invention. For example, while the forward orientation of the enhancer peptide sequence "WMEWDREI" (SEQ ID NO:4) is depicted below, its reverse orientation (i.e., "IERDWEMW"), (SEQ ID NO:49) although not depicted in Table II, below, is also an enhancer peptide sequence.

TABLE II

ENHANCER SEQUENCES

| | |
|---|---|
| WMEWDREI | IEWEWF |
| WQEWERKV | IEWEW |
| WQEWEQKV | EWEW |
| MTWMEWDREI | WASLWEWF |
| NNMTWMEWDREI | WAGLWEWF |
| WQEWEQKVRYLEANI | AKWASLWEWF |
| NNMTWQEWEZKVRYLEANI | AEWASLWEWF |
| WNWFI | WASLWAWF |
| WQEWDREISNYTSLI | AEWASLWAWF |
| WQEWEREISAYTSLI | AKWASLWAWF |
| WQEWDREI | WAGLWAWF |
| WQEWEI | AEWAGLWAWF |
| WNWF | WASLWAW |
| WQEW | AEWASLWAW |
| WQAW | WAGLWAW |
| WQEWEQKI | AEWAGLWAW |
| WASLWNWF | DKWEWF |
| WASLFNFF | IEWASLWEWF |
| WDVFTNWL | IKWASLWEWF |

TABLE II-continued

ENHANCER SEQUENCES

| | |
|---|---|
| WASLWEWF | DEWEWF |
| EWASLWEWF | GGWASLWNWF |
| WEWF | GGWNWF |
| EWEWF | |

It is understood that such enhancer polypeptide sequences can exhibit amino acid substitutions, deletions and/or insertions and discussed above for T20 and T1249 polypeptides.

5.2.2. SYNTHESIS OF T20 AND T1249 POLYPEPTIDES

The T20 and T1249 polypeptides of the invention, including the enhancer, core and hybrid polypeptides described supra, may be synthesized or prepared by techniques well known in the art for the synthesis and preparation of polypeptides in general. See, for example, Creighton, 1983, *Proteins: Structures and Molecular Principles*, W. H. Freeman and Co., New York, which is incorporated herein by reference in its entirety. For example, polypeptides may be prepared using conventional step-wise solution or solid phase synthesis, fragment condensation, F-MOC or T-BOC chemistry, as described, e.g., in *Chemical Approaches to the Synthesis of Peptides and Proteins*, William et al., Eds., 1997, CRC Press, Boca Raton Fla., and in references cited therein; in *Solid Phase Peptide Synthesis: A Practical Approach*, Atherton & Sheppard, Eds., 1989, IRL Press, Oxford, England, and in references cited therein; each of which is incorporated herein by reference in their entireties.

The polypeptides of the invention can be purified by art-known techniques such as normal and reverse phase high performance liquid chromatography, ion exchange chromatography, gel electrophoresis, affinity chromatography, size exclusion, precipitation and the like. The actual conditions used to purify a particular polypeptide will depend, in part, on synthesis strategy and on factors such as net charge, hydrophobicity, hydrophilicity, solubility, stability etc., and will be apparent to those having skill in the art.

Polypeptides used in the methods and compositions of the invention may also be made using recombinant DNA techniques. Here, the nucleotide sequences encoding the polypeptides of the invention may be synthesized, and/or cloned, and expressed according to techniques well known to those of ordinary skill in the art. See, for example, Sambrook, et al, 1989, *Molecular Cloning, A Laboratory Manual*, Vols. 1–3, Cold Spring Harbor Press, NY.

One may obtain the DNA segment encoding the polypeptide of interest using a variety of molecular biological techniques, generally known to those skilled in the art. For example, polymerase chain reaction (PCR) may be used to generate the DNA fragment encoding the protein of interest. Alternatively, the DNA fragment may be obtained from a commercial source.

The DNA encoding the polypeptides of interest may be recombinantly engineered into a variety of host vector systems that also provide for replication of the DNA in large scale. These vectors can be designed to contain the necessary elements for directing the transcription and/or translation of the DNA sequence encoding the hybrid polypeptide.

Vectors that may be used include, but are not limited to, those derived from recombinant bacteriophage DNA, plasmid DNA or cosmid DNA. For example, plasmid vectors such as pcDNA3, pBR322, pUC 19/18, pUC 118, 119 and the M13 mp series of vectors may be used. Bacteriophage vectors may include λgt10, λgt11, λgt18–23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors.

Alternatively, recombinant virus vectors including, but not limited to, those derived from viruses such as herpes virus, retroviruses, vaccinia viruses, adenoviruses, adeno-associated viruses or bovine papilloma viruses plant viruses, such as tobacco mosaic virus and baculovirus may be engineered.

In order to express a biologically active polypeptide, the nucleotide sequence coding for the protein may be inserted into an appropriate expression vector, i.e., a vector which contains the necessary elements for the transcription and translation of the inserted coding sequences. Methods which are well known to those skilled in the art can be used to construct expression vectors having the coding sequence of a polypeptide of interest operatively associated with appropriate transcriptional/translational control signals. These methods include in vitro recombinant DNA techniques and synthetic techniques. See, for example, the techniques described in Sambrook, et al., 1992, *Molecular Cloning, A Laboratory Manual*, Cold Spring Harbor Laboratory, N.Y. and Ausubel et al., 1989, *Current Protocols in Molecular Biology*, Greene Publishing Associates & Wiley Interscience, N.Y., each of which are incorporated herein by reference in its entirety.

Nucleic acid molecules encoding polypeptides of interest may be operatively associated with a variety of different promoter/enhancer elements. The promoter/enhancer elements may be selected to optimize for the expression of therapeutic amounts of protein. The expression elements of these vectors may vary in their strength and specificities. Depending on the host/vector system utilized, any one of a number of suitable transcription and translation elements may be used. The promoter may be in the form of the promoter which is naturally associated with the gene of interest. Alternatively, the DNA may be positioned under the control of a recombinant or heterologous promoter, i.e., a promoter that is not normally associated with that gene. For example, tissue specific promoter/enhancer elements may be used to regulate the expression of the transferred DNA in specific cell types.

Examples of transcriptional control regions that exhibit tissue specificity which have been described and could be used include, but are not limited to, elastase I gene control region which is active in pancreatic acinar cells (Swift et al., 1984, *Cell* 38:639–646; Omitz et al., 1986, *Cold Spring Harbor Symp. Quant. Biol.* 50:399–409; MacDonald, 1987, *Hepatology* 7:42S–51S); insulin gene control region which is active in pancreatic beta cells (Hanahan, 1985, *Nature* 315:115–122); immunoglobulin gene control region which is active in lymphoid cells (Grosschedl et al., 1984, *Cell* 38:647–658; Adams et al., 1985, *Nature* 318:533–538; Alexander et al., 1987, *Mol. Cell. Biol.* 7:1436–1444): albumin gene control region which is active in liver (Pinkert et al., 1987, *Genes and Devel.* 1:268–276) alpha-fetoprotein gene control region which is active in liver (Krumlauf et al., 1985, *Mol. Cell.*

*Biol.* 5:1639–1648; Hammer et al., 1987, *Science* 235:53–58); alpha-1-antitrypsin gene control region which is active in liver (Kelsey et al., 1987, *Genes and Devel.*

1:161–171); beta-globin gene control region which is active in myeloid cells (Magram et al., 1985, *Nature* 315:338–340; Kollias et al., 1986, *Cell* 46:89–94); myelin basic protein gene control region which is active in oligodendrocyte cells in the brain (Readhead et al., 1987, *Cell* 48:703–712); myosin light chain-2 gene control region which is active in skeletal muscle (Shani, 1985, *Nature* 314:283–286); and gonadotropic releasing hormone gene control region which is active in the hypothalamus (Mason et al., 1986, *Science* 234:1372–1378). Promoters isolated from the genome of viruses that grow in mammalian cells, (e.g. vaccinia virus 7.5K, SV40, HSV, adenoviruses MLP, MMTV, LTR and CMV promoters) may be used, as well as promoters produced by recombinant DNA or synthetic techniques.

In some instances, the promoter elements may be constitutive or inducible promoters and can be used under the appropriate conditions to direct high level or regulated expression of the nucleotide sequence of interest. Expression of genes under the control of constitutive promoters does not require the presence of a specific substrate to induce gene expression and will occur under all conditions of cell growth. In contrast, expression of genes controlled by inducible promoters is responsive to the presence or absence of an inducing agent.

Specific initiation signals are also required for sufficient translation of inserted protein coding sequences. These signals include the ATG initiation codon and adjacent sequences. In cases where the entire coding sequence, including the initiation codon and adjacent sequences are inserted into the appropriate expression vectors, no additional translational control signals may be needed. However, in cases where only a portion of the coding sequence is inserted, exogenous translational control signals, including the ATG initiation codon must be provided. Furthermore, the initiation codon must be in phase with the reading frame of the protein coding sequences to ensure translation of the entire insert. These exogenous translational control signals and initiation codons can be of a variety of origins, both natural and synthetic. The efficiency of expression may be enhanced by the inclusion of transcription attenuation sequences, enhancer elements, etc.

5.3 ADDITIONAL COMPONENTS

The carrier hydrogel composition (i.e., the hydrogel compositions) of the invention may also contain additional components such as one or more suitable pharmaceutically acceptable carriers. Such carriers include excipients and auxiliaries which facilitate processing or preparation of the bioactive molecules into a hydrogel composition as well as preservatives and/or stabilizers which keep the bioactive molecules from degrading. Exemplary excipients include, but are not limited to, sugars, including lactose, sucrose, trehalose, mannitol or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyroolidone (PVP). Other excipients and auxiliaries which may be used in the hydrogel compositions of the invention include concentrated sugar solutions, gum arabic, talc, polyvinyl pyrrolidone, carbopol gel, polyethylene glycol, titanium dioxide, lacquer solutions and suitable organic solvents or organic mixtures. Dyestuffs or pigments may also be included in the hydrogel compositions, e.g., for identification or to characterize different combinations of active compound dosages (i.e., dosages of bioactive molecules).

In instances where an enhancement of the patient's immune response is desired, the hydrogel compositions may also contain one or more suitable adjuvants in order to enhance the immunological response. Such adjuvants may include, but are not limited to, mineral gels such as aluminum hydroxide; surface active substances such as lysolecithin, pluronic polyols, polyanions; polypeptides, including polypeptides in addition to polypeptides which may be administered as therapeutic reagents; oil emulsions; and potentially useful adjuvants such as BCG and Carynebacterium parvum.

The hydrogel compositions may also contain emulsifying agents or substances which increase the viscosity, such as sodium carboxymethyl cellulose, sorbitol or dextran. Alternatively, ingredients such as ethanol may also be added to decrease viscoity. Optionally, the hydrogels may also contain suitable stabilizers or agents which increase the solubility of the bioactive molecules contained therein to allow, e.g., for the preparation of highly concentrated solutions. The hydrogel compositions may further contain different buffers, e.g., to modulate the salt concentration or pH of the compositions both in vitro (e.g., during storage as a liquid) and in vivo (e.g., when administered as a gel).

The carrier hydrogel compositions of the invention may further contain other bioactive molecules, including other therapeutic reagents, in addition to the T20 and/or T1249 peptides or derivatives of the T20 and/or T1249 peptides described above. As used herein, a therapeutic agent is any bioactive molecule, including but not limited to proteins, peptides, and antibodies as well as small molecules that exhibit biological activity and may be used to curve, ameliorate or prevent a disease or disease state in a patient, or to cure, ameliorate or prevent a symptom of a disease or disease state in a patient.

For example, the carrier hydrogel compositions may also contain one or more therapeutic reagents for a different type of therapy, such as one or more anticancer reagents as part of an anticancer therapy. In other embodiments, the carrier hydrogel compositions of the invention may contain a T20 or T1249 peptide or a derivative thereof and at least one, more preferably at least two, other antiviral reagents. Other antiviral reagents which may be used in the compositions of the invention, either by themselves or as part of a combinatorial therapy regime, include but are not limited to DP107 (T21), DP178 (T20) or any other polypeptide depicted from Table II, above, or derived therefrom. Other exemplary, non-limiting examples of therapeutic reagents include antiviral agents such as cytokines, e.g., rIFN α, rIFN β, rIFN γ; inhibitors of reverse transcriptase, including nucleoside and non-nucleoside inhibitors, e.g., AZT, 3TC, d4T, ddI, adefovir, abacavir and other dideoxynucleosides or dideoxyfluoronucleosides, or delaviridine mesylate, nevirapine, efavirenz; inhibitors of viral mRNA capping, such as ribavirin; inhibitors of HIV protease, such as ritonavir, nelfinavir mesylate, amprenavir, saquinavir, saquinavir mesylate, indinavir or ABT378, ABT538 or MK639; amphotericin B as a lipid-binding molecule with anti-HIV activity; and castanospermine as an inhibitor of glycoprotein processing.

5.4. METHODS OF USE

The compositions of the invention are most preferably used to administer T20 and T1249 polypeptides to patients. For example, an sufficient concentration or amount of T20 or T1249 may be dissolved, suspended or dispersed in a hydrogel composition of the invention while such hydrogel composition is cooled or chilled to a temperature below the gelation temperature and is in a liquid or fluidic state. The hydrogel composition, with a sufficient amount of T20 or T1249 dissolved, suspended or dispersed therein, may then be administered to a patient or it may be stored, preferably at a temperature below the gelation temperature, e.g., so that it may be administered to a patient at some later time.

The hydrogel composition may be administered to a patient, e.g., by subcutaneous, intramuscular, or intraperitoneal. Upon injection, the body heat of the patient then preferably heats the composition to a temperature above the gelation temperature so that the composition forms a gel depot of the polymer material with the T20 or T1249 polypeptides embedded therein. An effective dose of the polypeptides is thereby released from the polymer at a sustained rate.

The compositions of the invention can thus be used as part of methods for treating a disease state or conditions by administering an effective dose of a T20 or T1249 peptide to a patient. For example, in preferred embodiments the compositions of the invention are used to administer T20 and/or T1249 as part of methods for decreasing viral infection or of decreasing or inhibiting viral-induced events such as cell fusion. Most preferably, such antiviral methods are utilized against HIV (human immunodeficiency virus), e.g., HIV-1 and HIV-2, and SIV.

The carrier hydrogel composition of the present invention may further, be utilized to administer prophylactic agents for the prevention of disease, including the prevention of HIV infection or of diseases, such as AIDS (Acquired immunodeficiency Syndrome), that are associated with HIV infection. For example, the carrier hydrogel compositions may comprise and administer T20 or T1249 polypeptides that act to prevent HIV infection For all such treatments described above, the exact formulation and dosage (i.e., the exact amount of the peptide in the carrier hydrogel composition and/or the amount of the carrier hydrogel composition administered to a patient) can be chosen by the individual physician in view of the patient's condition. (See, e.g., Fingl et al., 1975, in *The Pharmacological Basis of Therapeutics*, Chpt. 1, page 1). It should be noted that the attending physician would know how to and when to terminate, interrupt or adjust administration due, e.g., to toxicity or organ dysfunctions. Conversely, the attending physician would also know to adjust treatment to higher levels (e.g., higher dosages or more frequent administration) if the clinical responses are not adequate (precluding toxicity). The magnitude of an administered dose in the management of the disorder of interest will vary with the severity of the condition to be treated and the route of administration. The dose and perhaps dose frequency will also vary according to the age, body weight and response of the individual patient. A program comparable to that discussed above may be used in veterinary medicine as well as for the treatment of human patients.

5.4.1. COMBINATORIAL THERAPY

The compositions of the invention may also be used to administer more than one therapeutic agent, e.g., as part of a combinatorial therapy regimen. Accordingly, the present invention also encompasses embodiments wherein the hydrogel compositions comprise T20, T1249 or a derivative thereof and at least one other therapeutic. For example, administration of different types of therapy can be performed concomitantly using the methods and compositions of the invention. In such embodiments, the carrier hydrogel composition will preferably contain at least one therapeutic reagent for administration as part of each of the different types of therapy. Thus, by way of example and not by way of limitation, in certain embodiments the carrier hydrogel composition may be used, e.g., to concomitantly administer T20, T1249 or a derivative thereof and an anticancer reagent as part of an anticancer therapy.

In other embodiments, the carrier hydrogel composition of the invention may contain a T20 or T1249 peptide and at least one, more preferably at least two, other antiviral reagents. Other antiviral reagents which may be used in the compositions of the invention, either by themselves or as part of a combinatorial therapy regime, include but are not limited to DP107 (T21), DP178 (T20) or any other polypeptide depicted from Table II, above, or derived therefrom. Other exemplary, non-limiting examples of therapeutic reagents include antiviral agents such as cytokines, e.g., rIFN α, rIFN β, rIFN γ; inhibitors of reverse transcriptase, including nucleoside and non-nucleoside inhibitors, e.g., AZT, 3TC, d4T, ddI, adefovir, abacavir and other dideoxynucleosides or dideoxyfluoronucleosides, or delaviridine mesylate, nevirapine, efavirenz; inhibitors of viral mRNA capping, such as ribavirin; inhibitors of HIV protease, such as ritonavir, nelfinavir mesylate, amprenavir, saquinavir, saquinavir mesylate, indinavir or ABT378, ABT538 or MK639; amphotericin B is a lipid-binding molecule with anti-HIV activity; and castanospermine as an inhibitor of glycoprotein processing.

5.4.2. EFFECTIVE DOSE

An effective dose of a therapeutic reagent such as T20, T1249 or derivatives thereof refers to an amount of the compound sufficient to result in amelioration of symptoms or a prolongation of survival in a patient as or when the compound is administered, e.g., in a sustained release composition such as the carrier hydrogel compositions of the present invention. Effective dosages of the therapeutic reagents, including polypeptides, to be administered using the hydrogel compositions of the invention may be determined through procedures well known to those in the art which address such parameters as biological half-life, bioavailability, and toxicity. In particularly preferred embodiments, an effective dose range is determined by one skilled in the art using data from routine in vitro and in vivo studies well known to those skilled in the art. For example, in vitro cell culture assays, such as the assays for antiviral activity described, e.g., in International Publication Nos. WO 94/28920 and WO 96/19495 (each of which is incorporated herein by reference in its entirety), will provide data from which one skilled in the art may readily determine the mean inhibitory concentration (IC) of the polypeptide necessary for some level of activity (e.g., to block some amount of viral infectivity such as 50%, $IC_{50}$; or 90%, $IC_{90}$). Appropriate doses can then be selected by one skilled in the art using pharmacokinetic data from one or more routine animal models, such as the exemplary pharmacokinetic data described in Sections 7–8 below, so that a minimum plasma concentration ($C_{min}$) of the peptide is obtained which is equal to or exceeds the determined IC value. In particular, pharmacokinetic data such as the data described below in Sections 7–8 can be used to extract a sufficient amount of T20 and T1249 (or of a T20 or T1249 derivative) to administer in a carrier hydrogel composition of the invention in order for an effective dose of the peptide to be released from the carrier hydrogel.

In those embodiments wherein the therapeutic reagent is a peptide, exemplary effective dosages may be as low as 0.1 μg/kg body weight and as high as 10 mg/kg body weight.

More preferably, an effective dosage range in such embodiments will be from 0.1 –100 µg/kg body weight. Other exemplary dosages for peptides include 1–5 mg, 1–10 mg, 1–30 mg, 1–50 mg, 1–75 mg, 1–100 mg, 1–125 mg, 1–150 mg, 1–200 mg or 1–250 mg of peptide.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is known as the therapeutic index and can be expressed as the ratio $LD_{50}/ED_{50}$. Compounds which exhibit large therapeutic indices are preferred. The data obtained from such cell culture assays and animal studies can be used in formulating a range of effective dosages for use in humans. The dosage of such compounds lies preferably within a range of circulating concentrations that include the $ED_{50}$ with little or no toxicity. The dose may vary within this range depending upon the dosage form employed and the route of administration utilized. For any compound administered as part of the methods and compositions of this invention (i.e., for any therapeutic reagent), the therapeutically effective dose can be estimated initially from cell culture assays. A dose may be formulated in animal models to achieve a circulating plasma concentration range that includes the $IC_{50}$ as determined in cell culture. Such information can be used to more accurately determine useful doses in humans. Levels in plasma may be measured, for example, by high performance liquid chromatography (HPLC) or by any biological or immunological assay capable of measuring levels of a therapeutic reagent such as peptide levels.

The methods and compositions of the invention may be used to administer T20, T1249 or derivatives thereof intermittently, periodically or continuously. For example, the hydrogel compositions of the invention may be used to administer therapeutic reagents in a single administration such as a single subcutaneous, intramuscular or intraperitoneal injection or infusion. The hydrogel compositions of the invention may also be used to administer therapeutic reagents in a plurality of intermittent administrations, including periodic administrations. For example, in certain embodiments a T20 or T1249 polypeptide can be administrated annually (i.e., once a year), semiannually (i.e., once every six months), once a trimester (i.e., once every 4 months), once a quarter (i.e., once every 3 months), bimonthly (i.e., once every two months) or once a month. A T20 or T1249 polypeptide may also be administered more frequently using the methods and compositions of the invention, such as once a week, once a day, twice a day (e.g., every 12 hours), every six hours, every four hours, every two hours, or every hour. A particular advantage of the compositions and methods of the present invention is that T20 and T1249 polypeptides administered by means of these methods and compositions have improved pharmacokinetics and bioavailability and therefore, require less frequent dosing. Accordingly, longer periods of administration are generally preferred. For example, in preferred embodiments T20 or T1249 peptides are administered using the methods and compositions of the invention no more frequently then twice a day, more preferably no more frequently than once a day. Still, more preferably, T20 or T1249 peptides are administered to a patient using the methods and compositions of the invention no more frequently than once every two days, once every three days, once every four days, once every five days, or once a week.

6. EXAMPLE: PREPARATION AND ANALYSIS OF EXEMPLARY HYDROGELS

The following example is offered by way of illustration, and not limitation, of the compositions and methods of the present invention. In particular, the example describes certain particular embodiments of the hydrogel compositions of the present invention. The physical properties of the compositions are also described, demonstrating that the compositions have properties useful for the administration of bioactive molecules such as polypeptides.

6.1. MATERIALS AND METHODS

Preparation of Hydrogels:

Exemplary hydrogel formations were prepared for subsequent characterization and analysis. Specifically, five different hydrogel formations, identified herein as F1, F2, F3, F4 and F5, were prepared using Poloxamer 407™ (Pluronic F-127™, BASF Company, Wyandotte, Mich.) as the gel-forming polymer material. The exact composition of each of these hydrogel formations is listed in Table III, below.

TABLE III

| Ingredient | F1 (% w/w) | F2 (% w/w) | F3 (% w/w) | F4 (% w/w) | F5 (% w/w) |
|---|---|---|---|---|---|
| Pluronic F-127 ™ | 20 | 20 | 30 | 30 | 20 |
| Absolute Ethanol | 10 | — | — | — | — |
| Sucrose | — | 5 | — | 5 | — |
| Water | 70 | 75 | 70 | 65 | 80 |

Four exemplary hydrogel formations were also prepared using methyl cellulose (Methocel™ A, Dow Chemical Company, Midland, Mich.) as the gel forming polymer material. Each of these hydrogel formations contained 5% w/w Methocel™ A (15LV) and 50 mM of Tromethamine Buffer (i.e., 50 mM tromethamine with sodium hydroxide and hydrochloric acid to adjust pH) pH 7.4, Tromethamine Buffer pH 8.4, Phosphate Buffer pH 7.4, or Phosphate Buffer pH 8.4, respectfully. The details of these gel compositions are provided in Table IV.

TABLE IV

| Ingredient | | | | |
|---|---|---|---|---|
| Methocel A 15LV | 5% w/w | 5% w/w | 5% w/w | 5% w/w |
| Tromethamine Buffer pH 7.4 | 50 mM | — | — | — |
| Tromethamine Buffer pH 8.4 | — | 50 mM | — | — |
| Phosphate Buffer pH 7.4 | — | — | 50 mM | — |
| Phosphate Buffer pH 8.4 | — | — | — | 50 mM |
| Water | qs* | qs | qs | qs |

*qs = quantum sufficit

Preparation of T20 in Hydrogels:

One vial of lyophilized T20 peptide was added to a specified volume of the F2 and F5 hydrogel formations to obtain final T20 concentrations of 25 mg/mL or 50 mg/mL, as listed below in Table V. Each vial of T20 peptide contained 50 mg of T20, 5.3 mg of sodium carbonate (anhydrous), 25 mg of mannitol, and sodium hydroxide/hydrochloric acid to adjust the pH to 8–9.

TABLE V

| Ingredient | F1-25 mg T20 | F2-25 mg T20 | F2-50 mg T20 | F5-25 mg T20 |
|---|---|---|---|---|
| Hydrogel formation | 2 ml of F1 | 2 mL of F2 | 1 mL of F2 | 2 mL of F5 |
| T20 | 1 vial | 1 vial | 1 vial | 1 vial |

Preparation of T20 for Intravenous Injection:

A Non-hydrogel preparation of T20 peptide was also prepared as a control by adding one vial of the above-described lyophilized T20 product to 2 mL of water for injection (USP) resulting in a 25 mg/mL aqueous solution of T20 peptide.

Hydrogel Stability Analysis:

Samples of the hydrogel formations were stored for a period of 15 days at 5, 25, and 37° C. The gel formation properties and stability of each hydrogel was examined periodically by analysis of (1) physical appearance, (2) pH, and (3) HPLC analysis of the formations immediately after preparation (0 days) and at time intervals of one, two, four, seven, fourteen, and fifteen days after preparation. For HPLC analysis, the samples were refrigerated at 4° C. for approximately 30 minutes and gently mixed. 10 µL aliquots were pipetted from the samples and transferred to a 1250 µL mobile phase.

6.2. RESULTS

PLURONIC F-127™ hydrogel formulations, identified as F1, F2, F3, F4, and F5, were prepared as described above. Carrier hydrogel composition were prepared from these compositions by adding 1 vial containing 50 mg of lyophilized T20 peptide to a volume of the gel formulations resulting in the following exemplary carrier hydrogel composition:

F1–25: 25 mg/mL T20, 20% PLURONIC F-127™, 10% ethanol (w/w);

F2–25: 25 mg/mL T20, 20% PLURONIC F-127™, 5% sucrose (w/w);

F2–50: 50 mg/mL T20, 20% PLURONIC F-127™, 5% sucrose (w/w); and

F5–25: 25 mg/mL T20, 20% PLURONIC F-127™ (w/w).

A control sample was also prepared, as described above, comprising of 25 mg/mL lyophilized T20 in water for injection (WI-25) with no hydrogel-forming polymer.

The physical properties of each pharmaceutical composition were examined over a 15 day period in samples stored at 5°, 25° and 37° C. Specifically, the physical appearance and pH of each sample was measured over a period of several days after preparation. Samples were also examined by HPLC to analyze the amount of T20 peptide in the sample and determine the extent of peptide degradation over time.

The analyses revealed that the compositions are both physically and chemically stable at temperatures ranging from 5° C. to physiological temperatures (37° C.) for a period of a least two weeks. Samples stored at cool temperature (5° C.) remain clear solutions for at least fifteen days, whereas the compositions formed and remained a clear hydrogel at temperatures in the physiological range (37° C.). pH change in all samples was minimal. In all cases, the pH was within a range acceptable for administration as a pharmaceutical reagent (pH 7.6–8.42). Degredation of the T20 peptide was also minimal, with only slightly degradation in samples stored at 37° C. at the end of two weeks. Thus, the hydrogel compositions of the invention maintain their physical and chemical stability under physiological conditions and over a time period sufficient for the sustained release of bioactive molecules, including the sustained release of peptides such as T20 and T1249.

7. EXAMPLE: ADMINISTRATION OF T20 IN A SUSTAINED RELEASE HYDROGEL

The following example is offered by way of illustration, and not limitation, of the compositions and methods of the present invention. In particular, the example demonstrates a particular, preferred embodiment of the invention wherein the therapeutic peptide referred to as T20 (see Table II above) is administered in a hydrogel. The data presented in the example shows that the pharmacokinetic properties of T1249, including half-life and bioavailability, are greatly improved when the peptide is administered in a hydrogel compared to administration by subcutaneous injection of T20 alone.

7.1. MATERIALS AND METHODS

Pharmacokinetic Studies:

Pharmacokinetic studies were performed on 16 cannulated male Sprague-Dawley rats having an average weight of 0.230 kg (StdDev=0.008 kg). Specifically, the rats were divided randomly into four groups (Groups I–IV). The rats in Group I were each administered T20 at a concentration of 50 mg/mL in a higher viscosity gel system (i.e., of the F2–50 pharmaceutical composition described in Section 6.1, supra. The rats in Group II were each administered T20 at a concentration of 25 mg/mL in a higher viscosity gel system (i.e., of the F2–25 pharmaceutical composition described in Section 6.1, supra). The rats in Group III were each administered T20 at a concentration of 25 mg/mL in a lower viscosity gel system (i.e., of the F5–25 pharmaceutical composition described in Section 6.1, supra). The rats in Group IV were administered T20 at a concentration of 25 mg/mL in an aqueous buffer (i.e., the WI-25 pharmaceutical composition described supra) as a control. The rats in all of the groups received the T20 via a single subcutaneous bolus injection of 25 µL of the formulation on the right side of the abdomen through a $30G_{1/2}$ Gauge needle. Each group received a dose level of approximately 5 mg/kg (Group I) or 2.5 mg/kg (Groups II–IV). More specifically, the dosages received by the animals in Groups I–IV were 6.71 mg/kg, 2.90 mg/kg, 3.27 mg/kg and 2.78 mg/kg, respectfully. These dosages were selected to approximate the dose levels, on a mg/cm$^2$ basis, to be used in humans.

Blood plasma levels of T20 were measured from samples collected from the animals immediately after (0 hours) and 1, 2, 4, 8, 12, and 24 hours post-dosing.

Calculation of Pharmacokinetic Parameters:

Pharmacokinetic parameters were calculated from the data as follows: The terminal elimination phase half ($t_{1/2}$, terminal) was calculated using the equation 0.693/k, where k equals the terminal elimination rate constant and is determined from a log/linear regression of at least three data points from the plasma concentration-time curve. $C_{max}$ was defined as the highest observed concentration between 0 and 12 hours postdose, and $t_{max}$ is the collection time corresponding to $C_{max}$. The area under the plasma concentration-time curve from 0 to 12 hours postdose ($AUC_{(0-12)}$) was calculated using the trapezoidal rule. $AUC_{(0-\infty)}$ was calculated using the trapezoidal rule and extrapolated to infinity by dividing the last plasma concentration by the terminal elimination rate constant (k). PTF values (peak-trough fluctuations) were calculated using the equation $(C_{max}-C_{min})/C_{av}$. $C_{min}$ was defined as the concentration of T20 at 12 hours postdose, and Cav was calculated using the equation $AUC_{(0-12)}/12$.

7.2. RESULTS

The pharmacokinetics of T20 administered in hydrogel compositions were studied in Sprague-Dawley rats at various dosages and hydrogel compositions, and these results were compared to the pharmacokinetics of T20 administered by subcutaneous injection of an aqueous solution alone. The results are illustrated in FIGS. 1 and 2. Specifically, FIG. 1 shows a plots of the T20 plasma concentration levels during the first 12 hours of the investigation. Within 12 hours must of the T20 administered in an aqueous solution had already cleared the blood stream while levels of T20 administered by a hydrogel remained elevated. FIG. 2 plots plasma concentrations of T20 administered in a hydrogel over a 24 hour period. Pharmacokinetic parameters from each group are listed below in Table VI.

TABLE VI

| Parameter | Group I | Group II | Group III | Group IV |
|---|---|---|---|---|
| $t_{1/2,terminal}$ (hours) | 4.75 ± 0.285 | 4.27 ± 0.159 | 4.61 ± 0.618 | 2.19 ± 0.350 |
| $t_{max}$ (hours) | 4.00 | 4.00 | 4.00 | 1.33 ± 0.577 |
| $C_{max}$ (µg/mL) | 5.97 ± 0.499 | 2.83 ± 0.316 | 3.78 ± 0.751 | 1.55 ± 0.640 |
| $AUC_{(0-12)}$ (µg · h/mL) | 43.4 ± 4.48 | 19.6 ± 3.45 | 25.7 ± 6.14 | 5.87 ± 1.69 |
| $AUC_{(0-\infty)}$ (µg · h/mL) | 55.4 ± 9.15 | 24.8 ± 4.86 | 32.8 ± 9.71 | 6.08 ± 1.61 |
| PTF | 1.22 ± 0.3394 | 1.24 ± 0.204 | 1.40 ± 0.443 | 2.96 ± 0.430 |

Subcutaneous injection of T20 formulated in an aqueous buffer (Group IV) resulted in a group mean terminal elimination phase half-life value of 2.19 hours. By contrast, the group mean half-life values of T20 administered in a hydrogel was approximately twice as along, ranging between 4.27–4.75 hours depending on the exact hydrogel formulation and T20 dosage used. $t_{max}$ values (i.e., the time after administration at which T20 plasma levels reach maximum concentrations) for T20 administered by subcutaneous injection was approximately 2 hours, while the $t_{max}$ of T20 administered by a hydrogel is approximately 4 hours. Thus, the data indicates that there is a depot effect associated with administration of T20 in a hydrogel resulting in a longer, more sustained bioavailability.

Subcutaneous injection of the high viscosity hydrogel formulation of T20 resulted in linearity of pharmacokinetics within the dose range tested. This is evidence by the proportional increase in AUC with increasing dose, as well as the observation that $t_{1/2}$ is equivalent at both dose levels. In summary, therefore, administration of T20 as a subcutaneous injection of a hydrogel has the surprising effect of approximately doubling both the bioavailability and the half-life of T20.

8. EXAMPLE: ADMINISTRATION OF T1249 IN A SUSTAINED RELEASE HYDROGEL

The following example is offered by way of illustration, and not limitation, of the compositions and methods of the present invention. In particular, the example demonstrates a particular, preferred embodiment of the invention wherein the therapeutic peptide T1249 (see Table II above) is administered in a hydrogel. The data presented in the example shows that, as with T20, the pharmacokinetic properties of T1249, including half-life and bioavailability, are greatly improved when the peptide is administered in a hydrogel compared to administration by subcutaneous injection of T1249 alone.

8.1. MATERIALS AND METHODS

Preparation of T1249 Carrier Hydrogel Composition:

Carrier hydrogel compositions containing T1249 were prepared in both a hydrogel and aqueous compositions. A hydrogel composition was prepared by adding 12.5 mg of lyophilized T1249 to 1 mL of the F5 hydrogel formulation described above in Section 6. A pharmaceutical composition of T1249 in aqueous solution was also prepared by combining lyophilized T1249 (12.5 mg) to 2 mL of water for injection (USP). The contained 12.5 mg of T1249, 25 mg mannitol and sodium hydroxide/hydrochloric acid to adjust the pH to 6.5.

Pharmacokinetic Studies:

The T1249 carrier hydrogel composition were administered to Sprague-Dawley rats according to the protocol described in Section 7.1, above, for T20. The rats were divided randomly into two groups (Groups I and II). The rats in Group I were each administered the above-described hydrogel compositions containing T1249. The rats in Group II were each administered the above-described composition of T1249 in aqueous buffer as a control. Blood plasma levels of T1249 were measured from samples collected from the animals immediately after (0 hours) and 1, 2, 4, 8, 12, 24, 36 and 48 hours post-dosing.

Calculation of Pharmacokinetic Parameters:

Pharmacokinetic parameters were calculated from the data as described in Section 7.1, above.

8.2. RESULTS

The pharmacokinetics of T1249 in a hydrogel composition were studied by administering T1249 to Sprague-Dawley rats in a low viscosity hydrogel composition (Group I) and in aqueous solution (Group II) at a dosage of 12.5 mg/mL. Each animal received a dosage of approximately 1.25 mg/kg, which was selected to approximate the dose levels, on a mg/cm$^2$ basis, to be used in humans. Postdose blood plasma levels of T1249 are plotted in FIG. 3. Pharmacokinetic parameters were calculated for both groups and are listed in Table VII, below.

TABLE VII

| Parameter | Group I | Group II |
|---|---|---|
| $t_{1/2,terminal}$ (hours) | 3.37 ± 0.68 | 2.28 ± 0.122 |
| $t_{max}$ (hours) | 8.00 | 2.00 |
| $C_{max}$ (µg/mL) | 1.90 ± 0.334 | 3.32 ± 0.215 |
| $AUC_{(0-12)}$ (µg · h/mL) | 28.2 ± 5.64 | 18.3 ± 4.06 |
| $AUC_{(0-\infty)}$ (µg · h/mL) | 29.1 ± 5.20 | 18.4 ± 4.07 |
| PTF | 1.62 ± 0.086 | 4.44 ± 0.680 |

The results show that T1249, like T20, exhibits improved pharmacokinetic properties when administered in a hydrogel composition.

9. REFERENCES CITED

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A composition comprising:

(a) a polymer material that forms a hydrogel at physiological temperatures, and (b) a polypeptide having the amino acid sequence X-WQEWEQKITALLEQAQIQQEKNEYELQKLD KWASLWEWF-Z (SEQ ID NO.:2), wherein X comprises an amino group, an acetyl group, a 9-fluorenylmethoxy-carbonyl group, a T-butoxycarbonyl group, or a macromolecular carrier group; and Z comprises a carboxyl group, an amido group, a T-butoxycarbonyl group or a macromolecular carrier group.

2. The composition of claim 1 wherein said composition is a liquid at temperatures below physiological temperatures.

3. The composition of claim 2 wherein said composition is a liquid below 30° C.

4. The composition of claim 3 wherein said composition is a liquid below 25° C.

5. The composition of claim 4 wherein said composition is a liquid below 15° C.

6. The composition of claim 5 wherein said composition is a liquid below 10° C.

7. The composition of claim 6 wherein said composition is a liquid below 5° C.

8. The composition of claim 1 wherein the polymer material is a block copolymer comprising ethylene oxide and propylene oxide.

9. The composition of claim 8 wherein the block copolymer is present in an amount between 20 and 30% by weight.

10. The composition of claim 8 wherein the block copolymer is present in an amount of 20% by weight.

11. The composition of claim 8 wherein the block copolymer is present in an amount of 30% by weight.

12. The composition of claim 1 wherein the polymer material is methyl cellulose.

13. The composition of claim 12 wherein methyl cellulose is present in an amount of between 4% and 8% by weight.

14. The composition of claim 13 wherein methyl cellulose is present in an amount of 5% by weight.

15. The composition of claim 1 wherein said composition comprises at least one other therapeutic reagent.

16. The composition of claim 15 wherein the other therapeutic reagent is an antiviral reagent.

17. The composition of claim 16 wherein the antiviral reagent is another polypeptide.

18. The composition of claim 16 wherein the antiviral reagent is a cytokine.

19. The composition of claim 16 wherein the antiviral reagent is an inhibitor of reverse transcriptase.

20. The composition of claim 16 wherein the antiviral reagent is an inhibitor of viral mRNA capping.

21. A method for sustained release of a peptide in a patient comprising administering to the patient a composition comprising:

(a) a polymer material that forms a hydrogel at physiological temperatures, and (b) a polypeptide having the amino acid sequence X-WQEWEQKITALLEQAQIQQEKNEYELQKLD KWASLWEWF-Z (SEQ ID NO.:2)

such that the composition acts as a sustained release matrix for the polypeptide, and wherein X comprises an amino group, an acetyl group, a 9-fluorenylmethoxy-carbonyl group, a T-butoxycarbonyl group, or a macromolecular carrier group; and Z comprises a carboxyl group, an amido group, a T-butoxycarbonyl group or a macromolecular carrier group.

22. The method of claim 21 wherein the composition is a liquid at temperatures below physiological temperatures.

23. The method of claim 21 wherein the composition is administered to the patient in a liquid state by subcutaneous, intramuscular or intraperitoneal injection.

24. The method of claim 21 wherein the injection is subcutaneous.

25. A method for ameliorating a symptom associated with an HIV infection comprising administering to an HIV infected patient a pharmaceutical composition comprising:

(a) a polymer material that forms a hydrogel at physiological temperatures, and (b) a sufficient amount of a polypeptide having the amino acid sequence

X-WQEWEQKITALLEQAQIQQEKNEYELQKLD KWASLWEWF-Z (SEQ ID NO.:2)

such that an effective dose of the polypeptide is released from the polymer at a sustained rate, and wherein X comprises an amino group, an acetyl group, a 9-fluorenylmethoxy-carbonyl group, a T-butoxycarbonyl group, or a macromolecular carrier group; and Z comprises a carboxyl group, an amido group, a T-butoxycarbonyl group or a macromolecular carrier group.

26. The method of claim 25 wherein the pharmaceutical composition further comprises at least one other therapeutic reagent.

27. The method of claim 26 wherein the other therapeutic reagent is another antiviral agent.

28. The method of claim 27 wherein the antiviral reagent is another polypeptide.

29. The method of claim 25 wherein the antiviral reagent is a cytokine.

30. The method of claim 25 wherein the antiviral reagent is an inhibitor of reverse transcriptase.

31. The method of claim 25 wherein the antiviral reagent is an inhibitor of viral mRNA capping.

* * * * *

SEQUENCE LISTING

<160> NUMBER OF SEQ ID NOS: 49

<210> SEQ ID NO 1
<211> LENGTH: 37
<212> TYPE: PRT
<213> ORGANISM: Artificial Sequence
<220> FEATURE:
<223> OTHER INFORMATION: core polypeptide

<400> SEQUENCE: 1

Tyr Leu Thr Ser Leu Ile His Ser Leu Ile Glu Ser Gln Asn Gln
1               5                   10                  15

Gln Glu Lys Asn Glu Gln Glu Leu Leu Glu Leu Asp Lys Trp Ala Ser
            20                  25                  30

Leu Trp Asn Trp Phe
        35

<210> SEQ ID NO 2
<211> LENGTH: 39
<212> TYPE: PRT
<213> ORGANISM: Artificial Sequence
<220> FEATURE:
<223> OTHER INFORMATION: core polypeptide

<400> SEQUENCE: 2

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35

<210> SEQ ID NO 3
<211> LENGTH: 23
<212> TYPE: PRT
<213> ORGANISM: Artificial Sequence
<220> FEATURE:
<223> OTHER INFORMATION: core polypeptide

<400> SEQUENCE: 3

Thr Ala Leu Leu Glu Gln Ala Gln Ile Gln Gln Glu Lys Asn Glu Tyr
1               5                   10                  15

Glu Leu Gln Lys Leu Asp Lys
            20

<210> SEQ ID NO 4
<211> LENGTH: 8
<212> TYPE: PRT
<213> ORGANISM: Artificial Sequence
<220> FEATURE:
<223> OTHER INFORMATION: enhancer peptide

<400> SEQUENCE: 4

Trp Met Glu Trp Asp Arg Glu Ile
1               5

<210> SEQ ID NO 5
<211> LENGTH: 8
<212> TYPE: PRT
<213> ORGANISM: Artificial Sequence
<220> FEATURE:
<223> OTHER INFORMATION: enhancer peptide

```
<400> SEQUENCE: 5

Trp Gln Glu Trp Glu Arg Lys Val
 1               5

<210> SEQ ID NO 6
<211> LENGTH: 8
<212> TYPE: PRT
<213> ORGANISM: Artificial Sequence
<220> FEATURE:
<223> OTHER INFORMATION: enhancer peptide

<400> SEQUENCE: 6

Trp Gln Glu Trp Glu Gln Lys Val
 1               5

<210> SEQ ID NO 7
<211> LENGTH: 10
<212> TYPE: PRT
<213> ORGANISM: Artificial Sequence
<220> FEATURE:
<223> OTHER INFORMATION: enhancer peptide

<400> SEQUENCE: 7

Met Thr Trp Met Glu Trp Asp Arg Glu Ile
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: enhancer peptide

<400> SEQUENCE: 8

Asn Asn Met Thr Trp Met Glu Trp Asp Arg Glu Ile
 1               5                  10

<210> SEQ ID NO 9
<211> LENGTH: 15
<212> TYPE: PRT
<213> ORGANISM: Artificial Sequence
<220> FEATURE:
<223> OTHER INFORMATION: enhancer peptide

<400> SEQUENCE: 9

Trp Gln Glu Trp Glu Gln Lys Val Arg Tyr Leu Glu Ala Asn Ile
 1               5                  10                  15

<210> SEQ ID NO 10
<211> LENGTH: 19
<212> TYPE: PRT
<213> ORGANISM: Artificial Sequence
<220> FEATURE:
<223> OTHER INFORMATION: enhancer peptide

<400> SEQUENCE: 10

Asn Asn Met Thr Trp Gln Glu Trp Glu Glx Lys Val Arg Tyr Leu Glu
 1               5                  10                  15

Ala Asn Ile

<210> SEQ ID NO 11
<211> LENGTH: 5
<212> TYPE: PRT
<213> ORGANISM: Artificial Sequence
<220> FEATURE:
<223> OTHER INFORMATION: enhancer peptide
```

```
<400> SEQUENCE: 11

Trp Asn Trp Phe Ile
 1               5

<210> SEQ ID NO 12
<211> LENGTH: 15
<212> TYPE: PRT
<213> ORGANISM: Artificial Sequence
<220> FEATURE:
<223> OTHER INFORMATION: enhancer peptide

<400> SEQUENCE: 12

Trp Gln Glu Trp Asp Arg Glu Ile Ser Asn Tyr Thr Ser Leu Ile
 1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: enhancer peptide

<400> SEQUENCE: 13

Trp Gln Glu Trp Glu Arg Glu Ile Ser Ala Tyr Thr Ser Leu Ile
 1               5                  10                  15

<210> SEQ ID NO 14
<211> LENGTH: 8
<212> TYPE: PRT
<213> ORGANISM: Artificial Sequence
<220> FEATURE:
<223> OTHER INFORMATION: enhancer peptide

<400> SEQUENCE: 14

Trp Gln Glu Trp Asp Arg Glu Ile
 1               5

<210> SEQ ID NO 15
<211> LENGTH: 6
<212> TYPE: PRT
<213> ORGANISM: Artificial Sequence
<220> FEATURE:
<223> OTHER INFORMATION: enhancer peptide

<400> SEQUENCE: 15

Trp Gln Glu Trp Glu Ile
 1               5

<210> SEQ ID NO 16
<211> LENGTH: 4
<212> TYPE: PRT
<213> ORGANISM: Artificial Sequence
<220> FEATURE:
<223> OTHER INFORMATION: enhancer peptide

<400> SEQUENCE: 16

Trp Asn Trp Phe
 1

<210> SEQ ID NO 17
<211> LENGTH: 4
<212> TYPE: PRT
<213> ORGANISM: Artificial Sequence
<220> FEATURE:
<223> OTHER INFORMATION: enhancer peptide
```

```
<400> SEQUENCE: 17

Trp Gln Glu Trp
 1

<210> SEQ ID NO 18
<211> LENGTH: 4
<212> TYPE: PRT
<213> ORGANISM: Artificial Sequence
<220> FEATURE:
<223> OTHER INFORMATION: enhancer peptide

<400> SEQUENCE: 18

Trp Gln Ala Trp
 1

<210> SEQ ID NO 19
<211> LENGTH: 8
<212> TYPE: PRT
<213> ORGANISM: Artificial Sequence
<220> FEATURE:
<223> OTHER INFORMATION: enhancer peptide

<400> SEQUENCE: 19

Trp Gln Glu Trp Glu Gln Lys Ile
 1               5

<210> SEQ ID NO 20
<211> LENGTH: 8
<212> TYPE: PRT
<213> ORGANISM: Artificial Sequence
<220> FEATURE:
<223> OTHER INFORMATION: enhancer peptide

<400> SEQUENCE: 20

Trp Ala Ser Leu Trp Asn Trp Phe
 1               5

<210> SEQ ID NO 21
<211> LENGTH: 8
<212> TYPE: PRT
<213> ORGANISM: Artificial Sequence
<220> FEATURE:
<223> OTHER INFORMATION: enhancer peptide

<400> SEQUENCE: 21

Trp Ala Ser Leu Phe Asn Phe Phe
 1               5

<210> SEQ ID NO 22
<211> LENGTH: 8
<212> TYPE: PRT
<213> ORGANISM: Artificial Sequence
<220> FEATURE:
<223> OTHER INFORMATION: enhancer peptide

<400> SEQUENCE: 22

Trp Asp Val Phe Thr Asn Trp Leu
 1               5

<210> SEQ ID NO 23
<211> LENGTH: 8
<212> TYPE: PRT
<213> ORGANISM: Artificial Sequence
<220> FEATURE:
<223> OTHER INFORMATION: enhancer peptide

<400> SEQUENCE: 23
```

```
Trp Ala Ser Leu Trp Glu Trp Phe
 1               5
```

<210> SEQ ID NO 24
<211> LENGTH: 9
<212> TYPE: PRT
<213> ORGANISM: Artificial Sequence
<220> FEATURE:
<223> OTHER INFORMATION: enhancer peptide

<400> SEQUENCE: 24

```
Glu Trp Ala Ser Leu Trp Glu Trp Phe
 1               5
```

<210> SEQ ID NO 25
<211> LENGTH: 4
<212> TYPE: PRT
<213> ORGANISM: Artificial Sequence
<220> FEATURE:
<223> OTHER INFORMATION: enhancer peptide

<400> SEQUENCE: 25

```
Trp Glu Trp Phe
 1
```

<210> SEQ ID NO 26
<211> LENGTH: 5
<212> TYPE: PRT
<213> ORGANISM: Artificial Sequence
<220> FEATURE:
<223> OTHER INFORMATION: enhancer peptide

<400> SEQUENCE: 26

```
Glu Trp Glu Trp Phe
 1               5
```

<210> SEQ ID NO 27
<211> LENGTH: 6
<212> TYPE: PRT
<213> ORGANISM: Artificial Sequence
<220> FEATURE:
<223> OTHER INFORMATION: enhancer peptide

<400> SEQUENCE: 27

```
Ile Glu Trp Glu Trp Phe
 1               5
```

<210> SEQ ID NO 28
<211> LENGTH: 5
<212> TYPE: PRT
<213> ORGANISM: Artificial Sequence
<220> FEATURE:
<223> OTHER INFORMATION: enhancer peptide

<400> SEQUENCE: 28

```
Ile Glu Trp Glu Trp
 1               5
```

<210> SEQ ID NO 29
<211> LENGTH: 4
<212> TYPE: PRT
<213> ORGANISM: Artificial Sequence
<220> FEATURE:
<223> OTHER INFORMATION: enhancer peptide

<400> SEQUENCE: 29

```
Glu Trp Glu Trp
 1

<210> SEQ ID NO 30
<211> LENGTH: 8
<212> TYPE: PRT
<213> ORGANISM: Artificial Sequence
<220> FEATURE:
<223> OTHER INFORMATION: enhancer peptide

<400> SEQUENCE: 30

Trp Ala Ser Leu Trp Glu Trp Phe
 1               5

<210> SEQ ID NO 31
<211> LENGTH: 8
<212> TYPE: PRT
<213> ORGANISM: Artificial Sequence
<220> FEATURE:
<223> OTHER INFORMATION: enhancer peptide

<400> SEQUENCE: 31

Trp Ala Gly Leu Trp Glu Trp Phe
 1               5

<210> SEQ ID NO 32
<211> LENGTH: 10
<212> TYPE: PRT
<213> ORGANISM: Artificial Sequence
<220> FEATURE:
<223> OTHER INFORMATION: enhancer peptide

<400> SEQUENCE: 32

Ala Lys Trp Ala Ser Leu Trp Glu Trp Phe
 1               5                   10

<210> SEQ ID NO 33
<211> LENGTH: 10
<212> TYPE: PRT
<213> ORGANISM: Artificial Sequence
<220> FEATURE:
<223> OTHER INFORMATION: enhancer peptide

<400> SEQUENCE: 33

Ala Glu Trp Ala Ser Leu Trp Glu Trp Phe
 1               5                   10

<210> SEQ ID NO 34
<211> LENGTH: 8
<212> TYPE: PRT
<213> ORGANISM: Artificial Sequence
<220> FEATURE:
<223> OTHER INFORMATION: enhancer peptide

<400> SEQUENCE: 34

Trp Ala Ser Leu Trp Ala Trp Phe
 1               5

<210> SEQ ID NO 35
<211> LENGTH: 10
<212> TYPE: PRT
<213> ORGANISM: Artificial Sequence
<220> FEATURE:
<223> OTHER INFORMATION: enhancer peptide

<400> SEQUENCE: 35

Ala Glu Trp Ala Ser Leu Trp Ala Trp Phe
```

```
1               5              10
```

<210> SEQ ID NO 36
<211> LENGTH: 10
<212> TYPE: PRT
<213> ORGANISM: Artificial Sequence
<220> FEATURE:
<223> OTHER INFORMATION: enhancer peptide

<400> SEQUENCE: 36

```
Ala Lys Trp Ala Ser Leu Trp Ala Trp Phe
 1               5                  10
```

<210> SEQ ID NO 37
<211> LENGTH: 8
<212> TYPE: PRT
<213> ORGANISM: Artificial Sequence
<220> FEATURE:
<223> OTHER INFORMATION: enhancer peptide

<400> SEQUENCE: 37

```
Trp Ala Gly Leu Trp Ala Trp Phe
 1               5
```

<210> SEQ ID NO 38
<211> LENGTH: 10
<212> TYPE: PRT
<213> ORGANISM: Artificial Sequence
<220> FEATURE:
<223> OTHER INFORMATION: enhancer peptide

<400> SEQUENCE: 38

```
Ala Glu Trp Ala Gly Leu Trp Ala Trp Phe
 1               5                  10
```

<210> SEQ ID NO 39
<211> LENGTH: 7
<212> TYPE: PRT
<213> ORGANISM: Artificial Sequence
<220> FEATURE:
<223> OTHER INFORMATION: enhancer peptide

<400> SEQUENCE: 39

```
Trp Ala Ser Leu Trp Ala Trp
 1               5
```

<210> SEQ ID NO 40
<211> LENGTH: 9
<212> TYPE: PRT
<213> ORGANISM: Artificial Sequence
<220> FEATURE:
<223> OTHER INFORMATION: enhancer peptide

<400> SEQUENCE: 40

```
Ala Glu Trp Ala Ser Leu Trp Ala Trp
 1               5
```

<210> SEQ ID NO 41
<211> LENGTH: 7
<212> TYPE: PRT
<213> ORGANISM: Artificial Sequence
<220> FEATURE:
<223> OTHER INFORMATION: enhancer peptide

<400> SEQUENCE: 41

```
Trp Ala Gly Leu Trp Ala Trp
 1               5
```

```
<210> SEQ ID NO 42
<211> LENGTH: 9
<212> TYPE: PRT
<213> ORGANISM: Artificial Sequence
<220> FEATURE:
<223> OTHER INFORMATION: enhancer peptide

<400> SEQUENCE: 42

Ala Glu Trp Ala Gly Leu Trp Ala Trp
1               5

<210> SEQ ID NO 43
<211> LENGTH: 6
<212> TYPE: PRT
<213> ORGANISM: Artificial Sequence
<220> FEATURE:
<223> OTHER INFORMATION: enhancer peptide

<400> SEQUENCE: 43

Asp Lys Trp Glu Trp Phe
1               5

<210> SEQ ID NO 44
<211> LENGTH: 10
<212> TYPE: PRT
<213> ORGANISM: Artificial Sequence
<220> FEATURE:
<223> OTHER INFORMATION: enhancer peptide

<400> SEQUENCE: 44

Ile Glu Trp Ala Ser Leu Trp Glu Trp Phe
1               5                   10

<210> SEQ ID NO 45
<211> LENGTH: 10
<212> TYPE: PRT
<213> ORGANISM: Artificial Sequence
<220> FEATURE:
<223> OTHER INFORMATION: enhancer peptide

<400> SEQUENCE: 45

Ile Lys Trp Ala Ser Leu Trp Glu Trp Phe
1               5                   10

<210> SEQ ID NO 46
<211> LENGTH: 6
<212> TYPE: PRT
<213> ORGANISM: Artificial Sequence
<220> FEATURE:
<223> OTHER INFORMATION: enhancer peptide

<400> SEQUENCE: 46

Asp Glu Trp Glu Trp Phe
1               5

<210> SEQ ID NO 47
<211> LENGTH: 10
<212> TYPE: PRT
<213> ORGANISM: Artificial Sequence
<220> FEATURE:
<223> OTHER INFORMATION: enhancer peptide

<400> SEQUENCE: 47

Gly Gly Trp Ala Ser Leu Trp Asn Trp Phe
1               5                   10
```

-continued

```
<210> SEQ ID NO 48
<211> LENGTH: 6
<212> TYPE: PRT
<213> ORGANISM: Artificial Sequence
<220> FEATURE:
<223> OTHER INFORMATION: enhancer peptide

<400> SEQUENCE: 48

Gly Gly Trp Asn Trp Phe
 1              5

<210> SEQ ID NO 49
<211> LENGTH: 8
<212> TYPE: PRT
<213> ORGANISM: Artificial Sequence
<220> FEATURE:
<223> OTHER INFORMATION: enhancer peptide

<400> SEQUENCE: 49

Ile Glu Arg Asp Trp Glu Met Trp
 1              5
```